United States Patent [19]
Grubbs et al.

[11] Patent Number: 5,811,515
[45] Date of Patent: Sep. 22, 1998

[54] SYNTHESIS OF CONFORMATIONALLY RESTRICTED AMINO ACIDS, PEPTIDES, AND PEPTIDOMIMETICS BY CATALYTIC RING CLOSING METATHESIS

[75] Inventors: Robert H. Grubbs, South Pasadena, Calif.; Scott J. Miller, Wellsley, Mass.; Helen E. Blackwell, Pasadena, Calif.

[73] Assignee: California Institute of Technology, Pasadena, Calif.

[21] Appl. No.: 654,712

[22] Filed: May 29, 1996

Related U.S. Application Data

[60] Provisional application No. 60/000,153 Jun. 12, 1995, and provisional application No. 60/010,170, Jan. 17, 1996.

[51] Int. Cl.$^6$ .............................. C07K 5/00; C07K 7/00; C07K 17/00
[52] U.S. Cl. ..................... 530/330; 530/331; 530/333; 530/334; 530/338; 556/136
[58] Field of Search ..................................... 530/333, 334, 530/338, 330, 331; 556/136

[56] References Cited

U.S. PATENT DOCUMENTS

| | | | |
|---|---|---|---|
| 4,883,851 | 11/1989 | Grubbs et al. | 526/268 |
| 4,945,135 | 7/1990 | Grubbs et al. | 525/338 |
| 4,945,141 | 7/1990 | Grubbs et al. | 526/90 |
| 4,945,144 | 7/1990 | Grubbs et al. | 526/268 |
| 5,198,511 | 3/1993 | Brown-Wensley et al. | 526/113 |
| 5,296,566 | 3/1994 | Brown-Wensley et al. | 526/171 |
| 5,312,940 | 5/1994 | Grubbs et al. | 526/136 |
| 5,342,909 | 8/1994 | Grubbs et al. | 526/171 |
| 5,410,020 | 4/1995 | Ghadiri | 530/333 |

OTHER PUBLICATIONS

Burrell et al., Synthesis and Reactions of Ru(=CH$_2$) Cl (No)$_2$, A Stable Terminal MethyleneComplex and the Crystal Structure of Ru(CH$_2$PPF$_2$)$_2$ (n$^2$–C$_2$F$_4$Cl (N)) (PPH$_3$), J. Chem. Soc., Dalton Trans., 1991, pp. 609–614.

Ivin, K.J. "Olefin Metathesis", 1983, Academic Press, pp. vii–x, 34–36.

McGrath et al., "Aqueous Ring–Opening Metathesis Polymerization of 7–Oxancorbornene Derivatives Using Ruthenium Catalysts", 1990, pp. 525–536.

Novak et al., "Catalytic Organometalic Chemistry in Water: The Aqueous Ring–Opening Metathesis Polymerization of 7–Oxanorbornene Derivatives", 1988, JACS, vol. 110,pp. 7542–7543g.

Hillmyer et al., "The Aqueous Ring–Opening Metathesis Polymerization of exo–N–Methyl–7–oxabicyclo [2.2.1] hept–5–ene–2, 3–dicarbonximide" 1991,pp. 162–163.

Carter et al., "Review of the Chemistry of Cyclopropane Compounds", Apr. 20, 1964,pp. 497–525.

Schmidbaur et al., "Ylide Chemistry: An Account of Structural, Conformational and Redox Investigations" 1983m pp. 167–170.

"Metathesis of Functionalized Olefin", J. of Molecules Catalysis, 15 (1992), pp. 35–45.

Bruce et al., "Cyclopentadienyl–Ruthenium and—Osmium Chemistry. Some Reactions ofSubstituted Vinylidene Complexes," *J. Organometallic Chem.*171:C5–C8 (1979).

M.H.L. Green et al., "Carbene Complexes of Iron, Molybdenum, and Ruthenium: A NewRoute to Metal–Carbene Derivatives," *J. Chem. Soc.* (A) 794–797 (1971).

H. Le Bozec et al., "A New Route to Vinylcarbene Metal Complexes in One Step from2–Propyn–1–ols and Arene Ruthenium (||) Derivatives," *J. Chem. Soc.*Chem. Comm. 219–221(1989).

Grundy et al., "Migratory–Insertion Reactions of Osmium (II) Ethyl Complexes DerivedFrom an Osium (0) Ethylene Complex," *J. Organometallic Chem.*216:255–262 (1981).

Grundy et al., Propionyl Complexes of Ruthenium Derived From the Reaction of Ethylenewith RuHCl(CO)$_2$(PPh$_3$)$_2$ *J. Organometallic Chem.* 265:77–85 (1984).

Richard R. Schrock, Living Ring–Opening Metathesis Polymerization Catalyzed by Well–Characterized Transition- –Metal Alkylidene Complexes, Acc.Chem. Res. 1990, vol. 23, pp. 158–165.

Gregory C. Fu et al., "Catalytic Ring–Closing Metathesis of Functionalized Dienes by a Ruthenium Carbene Complex" Am. Chem Soc. 1993, pp. 9856–9857.

Robert H. Grubbs et al., Ring–Opening Metathesis Polymerization Catalysts Polymer Preprints 1994, 35(1), p. 688.

Marc A. Hillmyer et al., The ROMP of COD by a Well–Defined Metathesis Catalyst in the Presence of a Disfunctional Chain Transfer Agent: The Preparation of Hydroxy–Telechelic 1,4–Poly(butadiene). Polymer Preprints 1993, 34(2), pp. 388–389.

Marc A. Hillmyer et al., "Preparation of Hydroxytelechelic Poly(butadiene) via Ring–Opening Metathesis Polymerization Employing a Well–Defined Metathesis Catalyst" Am. Chem Soc. Macromolecules, vol. 26, No. 4, 1992, pp. 872–874.

(List continued on next page.)

*Primary Examiner*—Sheela Huff
*Attorney, Agent, or Firm*—Limbach & Limbach L.L.P.

[57] ABSTRACT

A method for synthesizing conformationally restricted amino acids, peptides, and peptidomimetics by ring closing metathesis. The method includes the steps of synthesizing a peptide precursor containing first and second unsaturated C—C bonds and contacting the peptide precursor with a RCM catalyst to yield a conformationally restricted peptide. Suitable peptide precursors may contain two or more unsaturated C—C bonds. These bonds may be olefinic bonds and may be contained in first and second alkenyl groups which may be allyl groups. The RCM catalyst may be a Ruthenium or Osmium carbene complex catalyst and more specifically, a Ruthenium or Osmium carbene complex catalyst that includes a Ruthenium or Osmium metal center that is in a +2 oxidation state, has an electron count of 16, and is pentacoordinated. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

36 Claims, No Drawings

OTHER PUBLICATIONS

SonBinh R. Nguyen et al., "Syntheses and Activities of New Single–Component Ruthenium–Based Olefin Metathesis Catalysts" J. Am. Chem Soc. 1993, 115, 9858–9859.

Scott J. Miller et al., "Synthesis of Confirmationally Restricted Amino Acids and Peptides Employing Olefin Metathesis" J. Am. Chem Soc. 1995, 5855–5856.

BioOrganic & Medicinal Chemistry, vol. 3, No. 4, pp. 337–359. (1995).

Paul D. Drumheller et al., "Polymer Networks with Grafted Cell Adhesion Peptides for Highly Biospecific Cell Adhesive Substrates", Analytical Biochemistry 222, 380–388 (1994).

Ruth F. Nutt, et al., "Useful Intermediates for Synthesis of Dicarba Analogues of Cystine Peptides: Selectively Protected $\alpha$–Aminosuberic Acid and a, $\alpha,\alpha'$–Diaminosuberic Acid of Defined Stereochemistry" J. Org. Chem. 1980, 45, 3078–3080.

Ruth F. Nutt, et al., Synthesis of Nonreducible Bicyclic Analogues of Somatostain, J. Am. Chem. Soc. 1980, 102, 6539–6545.

Joachim Gante Peptidomimetics—Tailored Enzyme Inhibitors, Angem. Chem. Int Ed. Engl. 1994, 33, 1699–1720.

Michael Kahn "Peptide Secondary Structure Mimetics" Tetrahedron Symposia–In–Print No. 50. pp. xi–xvii. (1993).

C. Toniolo "Conformationally Restricted Peptides Through Short–Range Cyclizations" Int. J. Peptide Protein Res. 35, 1990. 287–300.

Ramakanth Sarabu et al., "Design, Synthesis, and Three Dimensional Structural Characterizatio of a Constricted $\Omega$–Loop Excised from Interleukin–1$\alpha$" Tetrahedron, vol. 49 p. 3629 (1993).

SonBinh T. Nguyen et al., "Ring–Opening Metathesis Polymerization (ROMP) of Norbornene by a Group VIII Carbene Complex is Protic Media", J. Am. Chem. Soc. 1992, 114, 3974–3975.

Journal of the American Chemical Society, vol. 118, No. 40, pp. 9606–9614 entitled Application of Ring–Closing Metathesis to the Synthesis of Rigidified Amino Acids and Peptides, Scott J. Miller, et al. (1996).

Journal of the American Chemical Society, vol. 117, 1995, pp. 12364–12365. Supra Molecular Design by Covalent Capture. Design of a Peptide Cylinder via Hydrogen–Bond––Promoted Intermolecular Olefin Metathesis, Thomas D.Clark et al.

SYNTHESIS OF CONFORMATIONALLY RESTRICTED AMINO ACIDS, PEPTIDES, AND PEPTIDOMIMETICS BY CATALYTIC RING CLOSING METATHESIS

The U.S. Government has certain rights in this invention pursuant to Grant No. GM-31332 awarded by the NIH.

This application claims the benefit of U.S. Provisional application Ser. No. 60/000,153, filed Jun. 12, 1995, and U.S. Provisional application Ser. No. 60/010,170, filed Jan. 17, 1996.

BACKGROUND

The present invention generally relates to the synthesis of conformationally restricted amino acids and peptides. More specifically, the invention relates to the synthesis of conformationally restricted amino acids and peptides by catalyzed ring closing metathesis ("RCM").

Conformationally restricted peptides, amino acids, and peptidomimetics are becoming increasingly important in drug design and development. In the case of peptidomimetics, there have been numerous approaches to the design and synthesis of these molecules including methods based on side chain modification, amide linkage modification and de novo synthesis of particular structural motifs. These synthetic approaches and many uses of peptidomimetics are described in recent reviews by Joachim Gante (Angew. Chem. Int. Ed. Eng. 33 1699, 1994) and lwao Ojima et al. (Bioorganic and Medicinal Chemistry 3 337, 1995) both of which are incorporated herein by reference.

A common theme among many of the synthetic strategies has been the introduction of some cyclic moiety into a peptide-based framework. The cyclic moiety restricts the conformational space of the peptide structure and this frequently results in an increased affinity of the peptide for a particular biological receptor. An added advantage of this strategy is that the introduction of a cyclic moiety into a peptide may also result in the peptide having a diminished sensitivity to cellular peptidases.

To date there has been no general systematic method for introducing cyclic moieties into peptides. Conventional methods are usually specific to particular syntheses and cannot easily be generalized to other peptide systems. Furthermore, many of the conventional methods are cumbersome, many step syntheses and usually involve heteroatom containing cross-links, which are not as stable as carbon-carbon bond based cross-links. The majority of the existing synthetic methods employ harsh conditions which require the synthesis of the complete cross-link prior to its introduction into the peptide. See for example: J. F. Callahan et al, Tetrahedron Letters 32, 7203 (1991); R. F. Nult et al. J.Org. Chem. 45, 3078 (1980) and J.Am. Chem. Soc., 102, 6539 (1980); Tetrahedron Symposia-in-print Number 50, Tetrahedron 49, xi–xii (1933); C Tondio,lnt. J. Peptide Protein Res 35, 287 (1990); and R. Sarabu et al., Tetrahedron 49, 3629 (1993).

A drawback of using conventional ring-closing metathesis methods to synthesize conformationally restricted amino acids, peptides, and peptidomimetics is that many of the catalysts used are easily poisoned by the presence of functional groups. Since peptides necessarily contain a variety of functional groups including alcohols, thiols, amines, imines, amides, carboxylic acids, and disulfides many of the conventional ring-closing metathesis methodologies cannot therefore be used for the production of cyclic moiety containing peptidomimetics.

It is an object of the present invention to provide a method of synthesizing cyclic stabilized peptidomimetics that is both simple and easily generalizable to a wide variety of peptide structures. It is a further object of the invention to provide a method of synthesizing peptidomimetics that include cyclic moieties that are stabilized by carbon-carbon bond cross-links. It is also an object of the present invention to provide a method of introducing a cyclic moiety into a peptide that does not require the synthesis of the complete cross-link prior to its introduction into the peptide. It is yet another object of the invention to provide a method of synthesizing cyclic stabilized peptidomimetics that can be carried out in the presence of a variety of functional groups and in a variety of solvent systems.

SUMMARY OF THE INVENTION

The present invention meets the above needs by providing a method for synthesizing conformationally restricted peptides by ring closing metathesis. The method includes the steps of synthesizing a peptide precursor containing first and second unsaturated C—C bonds and contacting the peptide precursor with a RCM catalyst to yield a conformationally restricted peptide. Suitable peptide precursors may contain two or more unsaturated C—C bonds. The RCM catalyst may be a Ruthenium or Osmium carbene complex catalyst and more specifically, a Ruthenium or Osmium carbene complex catalyst that includes a Ruthenium or Osmium metal center that is in a +2 oxidation state, has an electron count of 16, and is pentacoordinated. The Ruthenium or Osmium carbene complex catalyst may be of the formula

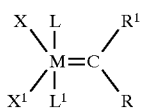

wherein: M is selected from the group consisting of Os and Ru; R and $R^1$ are independently selected from the group consisting of hydrogen and a functional group selected from the group consisting of $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, each functional group optionally substituted with $C_1$–$C_5$ alkyl, a halide, $C_1$–$C_5$ alkoxy or with a phenyl group optionally substituted with a halide, $C_1$–$C_5$ alkyl or $C_1$–$C_5$ alkoxy; X and $X^1$ are anionic ligands; and L and $L^1$ are neutral electron donors.

L and $L^1$ can be phosphines of the formula $PR^3R^4R^5$, where $R^3$ is selected from the group consisting of secondary alkyl and cycloalkyl, and $R^4$ and $R^5$ are independently selected from aryl, $C_1$–$C_{10}$ primary alkyl, secondary alkyl and cycloalkyl.

The catalyst may be

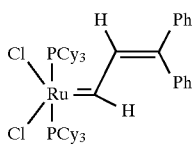

or

-continued

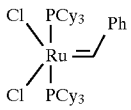

The method provided by the invention may also be used to synthesize conformationally restricted amino acids, conformationally restricted β-turns, and peptides containing conformationally restricted -Arginine-Glycine-Aspartic Acid- motifs ("RGD" motifs). The method may optionally include the following features:

First, the peptide precursor may contain one or more substituent functional groups selected from the group consisting of alcohol, thiol, ketone, aldehyde, ester, ether, amine, amide, imine, nitro acid, carboxylic acid, disulfide, carbonate, carboalkoxy acid, isocyanate, carbodiimide, carboalkoxy, and halogen.

Second, the first and second unsaturated C—C bonds may be olefinic bonds and may be contained in first and second alkenyl groups which may be allyl groups. The alkenyl groups may be directly bonded to an α-carbon or amine nitrogen of amino acids in the peptide precursor. These alkenyl group containing amino acids may be N-terminal or C-terminal amino acids. They may be glycine or a derivative of glycine.

Third, the peptide precursor may be a dipeptide, tripeptide, tetrapeptide, or pentapeptide.

Fourth, the peptide precursor may be contacted with the catalyst in the presence of protic, aqueous, or organic solvents, or mixtures thereof.

Fifth, the conformationally restricted peptide may be hydrogenated by being contacted with $H_2$ in the presence of a hydrogenation catalyst.

In another embodiment of the invention, the method of synthesizing conformationally restricted peptides by ring closing metathesis may be carried out using solid-phase-peptide-synthesis techniques. In this embodiment, a precursor, which is an amino acid or peptide containing first and second unsaturated C—C bonds and which is anchored to a solid support, is contacted with a RCM catalyst and the product is then cleaved from the solid support to yield a conformationally restricted peptide. The RCM catalyst and the optional features of the method may be the same as described above.

DETAILED DESCRIPTION OF THE INVENTION

The present invention is an application of catalyzed RCM to the synthesis of conformationally restricted amino acids, peptides, and peptidomimetics. These conformationally restricted molecules are useful where such conformationally restricted peptides are advantageous; for example, in drug design and delivery, as cell adhesion molecules, and as inhibitors of platelet aggregation.

The present invention involves the following general method for producing conformationally restricted amino acids, peptides, and peptidomimetics. The first step is to synthesize a peptide or amino acid precursor that is capable of undergoing catalyzed RCM. The second step is to catalyze a RCM reaction of the unsaturated C—C bonds in the precursor to yield the conformationally restricted product.

Suitable precursors include peptides and amino acids that include two or more unsaturated C—C bonds. By judicious placement of the unsaturated bonds in the precursor it is possible to control the size and geometry of the cyclic moiety in the conformationally restricted product. Below, we give specific examples of suitable precursors including details of their synthesis.

Suitable catalysts for use in the present invention include any catalyst capable of catalyzing the RCM of a peptide precursor. That is, any RCM catalyst that is not poisoned by the functional groups present in the peptide precursors. For example, suitable catalysts for use in the present invention include the ruthenium and osmium carbene complexes disclosed in U.S. Pat. Nos. 5,312,940 and 5,342,909, each of which is incorporated herein by reference.

Below, the general and preferred catalysts for use in the present invention are first described. Methods of preparing the required amino acid and peptide precursors are then described. Next, the RCM of these precursors to yield conformationally restricted amino acids, peptides, and peptidomimetics is described. Examples of conformationally restricted products include C—C bond cross-link stabilized β-turns and RGD motifs. After this, the hydrogenation of the peptidomimetics products of the RCM reactions to yield conformationally restricted peptides that are stabilized by unsaturated C—C bond cross-links is described. Finally, the application of Solid-Phase-Peptide-Synthesis ("SPPS") techniques to the RCM reaction of the present invention is described.

RCM Catalysts

Suitable catalysts for use in the present invention include stabilized, late transition metal carbene complex catalysts. Group VIII transition metal carbene catalysts are preferred and Ru and Os metal carbene catalysts are most preferred. An important feature of the preferred catalysts is that the Ru and Os metal centers are in the +2 oxidation state, have an electron count of 16, and are pentacoordinated.

The ligand environment around the metal center may include two anionic ligands and two neutral electron donating ligands. The anionic ligands may be any ligand which when removed from a metal center in its closed shell electron configuration has a negative charge. The electron donating ability of the neutral electron donating ligands influences the activity of the catalyst and in this way it is possible to fine-tune the metathesis activity of the catalysts. It is also possible to control the solubility of the carbene compounds by proper selection of either hydrophobic or hydrophilic ligands as is well known in the art. The stability of the catalysts in the presence of a wide variety of functional groups allows them to be used to catalyze reactions that are carried out in aqueous, protic, or organic solvents, or mixtures thereof.

The following preferred RCM catalysts may be used in the present invention

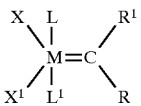

wherein: M is selected from the group consisting of Os and Ru; R and $R^1$ are independently selected from the group consisting of hydrogen and a functional group selected from the group consisting of $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, each functional group optionally substituted with $C_1$–$C_5$ alkyl, a halide, $C_1$–$C_5$ alkoxy or with a phenyl group optionally substituted with a halide, $C_1$–$C_5$ alkyl or $C_1$–$C_5$ alkoxy; X and $X^1$ are anionic ligands; and L and $L^1$ are neutral electron donors. More specifically, L and $L^1$ may be phosphines of the formula $PR^3R^4R^5$, where $R^3$ is selected from the group consisting of secondary alkyl and cycloalkyl, and $R^4$ and $R^5$ are independently selected from aryl, $C_1$–$C_{10}$ primary alkyl, secondary alkyl and cycloalkyl.

A preferred catalyst for use in the present invention is

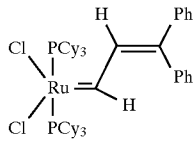

CATALYST 1 and the most preferred catalyst is

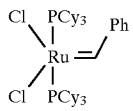

CATALYST 2 where Cy is cyclohexyl.

The catalysts used in the present invention may be prepared by a variety of different methods such as those taught in U.S. Pat. No. 5,312,940. The most preferred catalyst may be prepared using methods described by P. Schwab et al., J. Am. Chem. Soc. 118, 100 (1996), which is incorporated herein by reference.

Preparation of Peptide and Amino Acid Precursors

Suitable precursors for use in the present invention are any peptides or amino acids that are capable of undergoing RCM to yield a conformationally restricted peptide or amino acid.

Generally, any peptide or amino acid that contains two or more unsaturated C—C bonds is a suitable RCM precursor. We have discovered that precursors that include two alkenyl groups can be used in the present invention. However, if the product of the RCM reaction would contain a ring structure that is highly strained, other reactions pathways may take preference over the ring-closing reaction. For example, see the attempted synthesis of dehydro-proline described below. Furthermore, if the product of the RCM reaction contains a ring structure that is too flexible, the advantages of conformational restriction will be lost. In view of these criteria, peptides and amino acids that include two $C_2$–$C_{10}$ alkenyl groups are especially suitable precursors for the present invention. The alkenyl groups may optionally be substituted with a variety of functional groups including alcohol, thiol, ketone, aldehyde, ester, ether, amine, imine, amide, nitro acid, carboxylic acid, disulfide, carbonate, carboalkoxy acid, isocyanate, carbodiimide, carboalkoxy and halogen functional groups. More particularly, peptides and amino acids that include two allyl groups are suitable precursors for the present invention. The preferred precursors, which are exemplified below, include allyl groups introduced at the α-carbon or amide nitrogen of the amino acid residues.

The following two step strategy may be used for synthesizing the peptide precursors. The first step is to synthesize an amino acid which includes an alkenyl group substituted at either the α-carbon or amide nitrogen. This may be accomplished using the procedures shown below or using other conventional synthetic schemes. The second step is to incorporate two or more alkenyl substituted amino acids residues into a peptide chain. By incorporating the residues at specific locations in the peptide sequence the alkenyl groups which will undergo RCM may be placed so as to give the desired ring-closed product. The incorporation of the alkenyl substituted residues may be accomplished using conventional peptide coupling techniques and in this way, any peptide that can be synthesized using conventional peptide coupling techniques can also be synthesized to include the unsaturated C—C bonds needed for a subsequent RCM reaction.

Although any amino acid may be synthesized to include the unsaturated C—C bond, allyl substituted glycine is the preferred alkenyl substituted amino acid. One reason for this is that α-carbon substituted (+) and (–) allyl glycine is commercially available and amide nitrogen substituted allyl glycine is easily synthesized by the following method.

METHOD 1

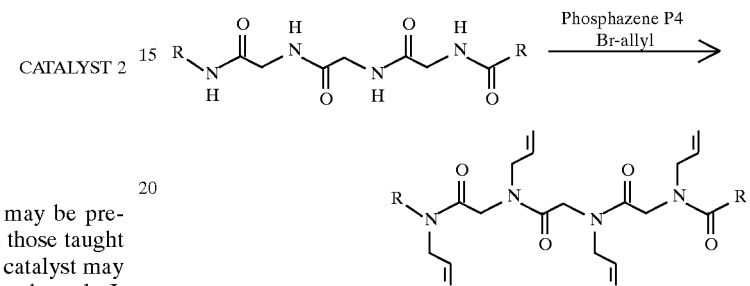

This is the "Seebach" method which was reported by Seebach in another context. The method is described in "N-Perbenzylation of Oligopeptides with P4-Phosphazene Base—A New Protecting Group Technique for Modification and Solubilization of Peptides in Apolar Organic Solvents" Angew. Chem. Int. Ed. Eng. 31, 1481 (1992), which is incorporated herein by reference. Amide nitrogen allyl substituted glycine may be recovered from the Seebach product by cleaving the amide linkages of the tripeptide using conventional methods.

Another method which may be used to incorporate an allyl group at the glycine amide nitrogen is as follows.

METHOD 2

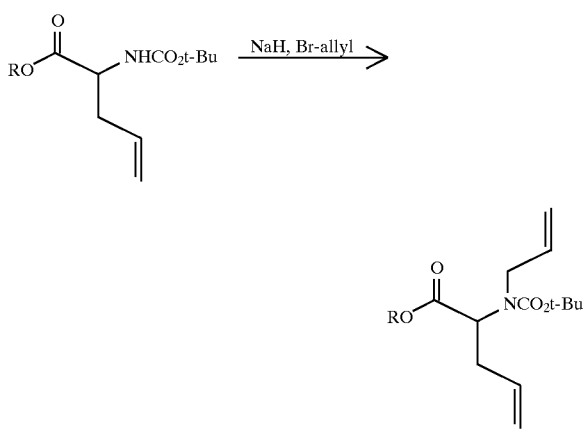

Treatment of a suitably protected amino acid with base, followed by allyl bromide affords N-allylated materials.

In addition to using allyl substituted glycine to incorporate the required unsaturated C—C bonds into the peptide precursors, it is also possible to use derivatives of naturally occurring amino acids. These precursors are easily synthesized using conventional techniques. For example, we have synthesized the Tyrosine Allyl Ether and Asparagine Allyl Amide show n below. The Serine and Aspartate derivatives are easily synthesized using well known techniques.

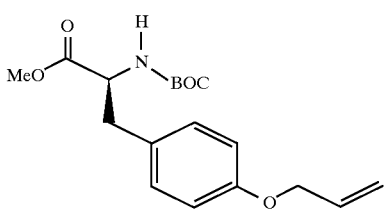

Tyrosine Allyl Ether

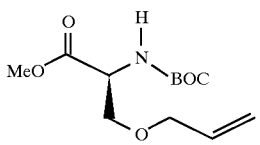

Serine Allyl Ether

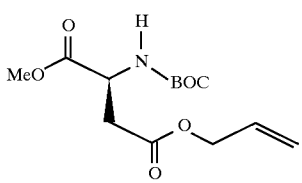

Aspartate Allyl Ester

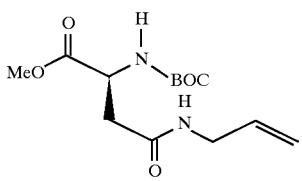

Asparagine Allyl Amide

Peptide precursors suitable for use in the present invention may include both standard and nonstandard amino acids. The standard amino acids include Glycine, Alanine, Valine, Leucine, Isoleucine, Proline, Phenylalanine, Tryptophan, Methionine, Serine, Threonine, Cysteine, Tyrosine, Asparagine, Glutamine, Aspartic acid, Glutamic acid, Lysine, Arginine and Histidine. There are over 700 known nonstandard amino acids any of which may be included in the peptide precursors for use in the present invention. See, for example S. Hunt, The Non-Protein Amino Acids: In Chemistry and Biochemistry of the Amino Acids, edited by G. C. Barrett, Chapman and Hall, 1985. Some examples of non-standard amino acids are β-Alanine, D-Alanine, 4-Hydroxy proline, Desmosine, D-Glutamic acid, γ-Aminobutyric acid, β-cyanoalanine, Norvaline, 4-(E)-Butenyl-4(R)-methyl-N-methyl-L-threomine, N-Methyl-L-leucine, and Statine.

The peptide precursors suitable for use in the present invention may be derivatized to include amino acid residues that are hydroxylated, phosphorylated, sulfonated, glycosylated, and disulfide bonded. In addition, the stability of RCM catalysts to functional groups allows peptide precursors to be used in the present invention that include alcohol, thiol, ketone, aldehyde, ester, ether, amine, imine, amide, nitro acid, carboxylic acid, disulfide, carbonate, carboalkoxy acid, isocyanate, carbodiimide, carboalkoxy and halogen functional groups.

The examples shown below demonstrate that RCM may be used to produce both amino acid and peptide based conformationally restricted peptidomimetics. In these examples the reactants and products are shown in their protected form. The unprotected end product is easily obtained from the protected reaction product using standard deprotection techniques.

RCM Synthesis of Conformationally Restricted Amino Acids and Peptides Containing 6, 7, and 8 Membered Rings The following general experimental procedure was used for the RCM reactions described in this and subsequent sections. Detailed descriptions of precursor synthesis and RCM reaction conditions are given in the final, "Experimental Procedures" Section.

Catalyst 1 ($Cl_2(PCy_3)_2Ru{=}CHCH{=}CPh_2$) (ca. 5 mol %) in $CH_2Cl_2$ (10 mL) is added through a cannula to a solution of the precursor (0.30 mmol) in $CH_2Cl_2$ (10 mL, 0.015M concentration for the reaction mixture). The resulting solution is placed in a 50° C. oil bath. The reaction is monitored by thin layer chromatography (TLC) and upon completion is filtered through a short silica plug to remove metal salts. The solution is concentrated under reduced pressure and purified by flash chromatography to afford the ring-closed products. Compounds are identified on the basis of their $^1H$ NMR, $^{13}C$ NMR, IR, and Mass Spectral characteristics.

Equation 1 shows the RCM of an amino acid precursor to give a conformationally restricted glycine product containing a 6-membered ring. Treatment of the modified glycine amino acid 2 under the conditions described above afforded the dehydro-pipicolinate 5 in good yield (90%) within 1 h.

EQUATION 1

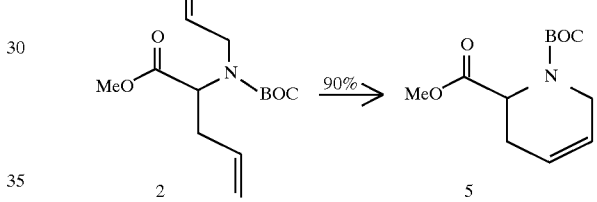

Equations 2 and 3 show the RCM of dipeptide precursors to yield conformationally restricted products which include 7 and 8 membered rings respectively. Precursors 3 and 4 required more stringent conditions than precursor 2, and the isolated yields were somewhat lower. Nevertheless, the seven-membered ring 6 can be obtained in 50% yield from the peptide precursor 3 and the eight-membered ring 7 can be obtained in 51% from the peptide precursor 4. Each of these latter transformations appear to be limited by the inherent ring strain of the product, which necessitates that the reactions be run at higher dilution to minimize competing intermolecular oligomerization processes.

EQUATION 2

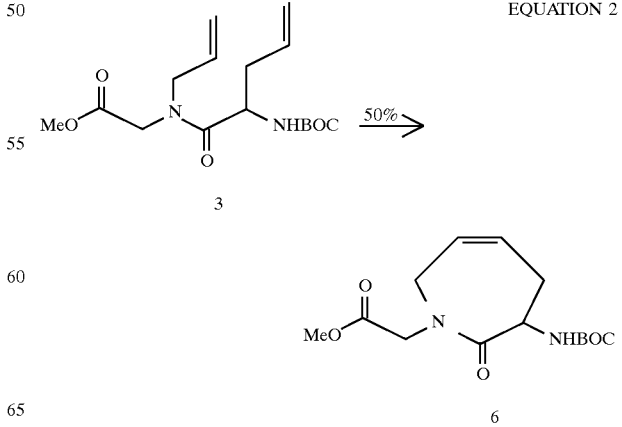

EQUATION 3

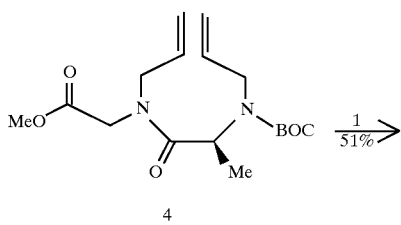

a) NaH, allyl-Br, DMF  b) NaIO$_4$, THF/H$_2$O
c) ClPh, 130° C., CaCO$_3$  d) 1.

RCM in Presence of Free Amide —NH Groups.

Equation 5 shows the RCM of a precursor that includes free amide NH-groups. Tripeptide precursor 10 was prepared by conventional peptide coupling and allylation chemistry and was then treated under conditions exactly analogous to those of Equation 1. The RCM reaction afforded peptidomimetic 11 in 81% yield. This example illustrates that the RCM reaction of the present invention may be carried out in the presence of unprotected peptidic structures.

RCM Synthesis of Peptidomimetics Containing a 5 Membered ring

Equations 1–3 above show that the RCM reactions of the present invention may be used to produce conformationally restricted amino acids and peptides containing six, seven and eight-membered rings. Equation 4 shows the result of our attempt to synthesize a peptidomimetic containing a dehydro-proline derivative five membered ring. Vinyl glycine derivative 8 was prepared by a modification of Rapoport's procedure, see Carrasco et al, Org. Synth. 70, 29 (1992). However, the RCM reaction employing precursor 8 and conditions analogous to those of Equation 1 afforded no dehydro-proline derivatives, and only the dehydro amino acid 9 was isolated. The mechanism of this side reaction is a matter of debate, however, the enhanced acidity of the allylic α-carbon proton is likely at the heart of the problem.

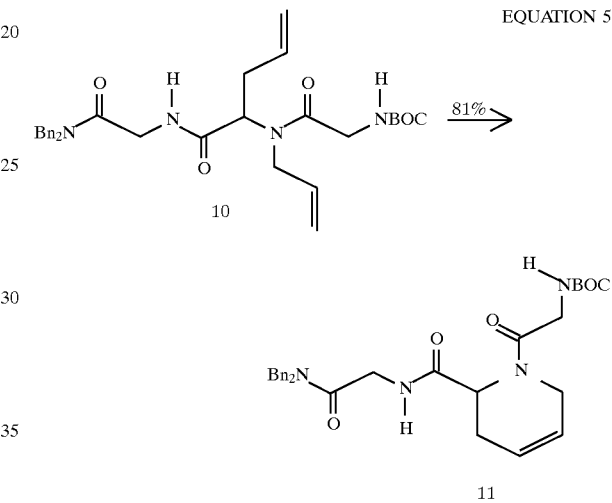

EQUATION 5

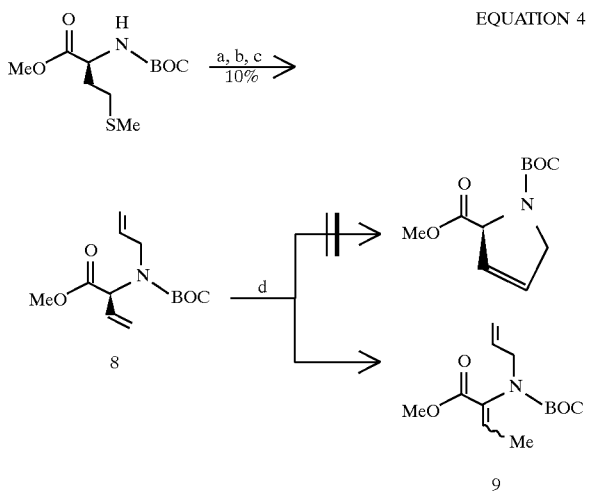

EQUATION 4

RCM Using Allyl Substituted Amino Acids Other Than Glycine

The present invention can use precursors other than allyl substituted glycine. To demonstrate this we have carried out RCM using precursors that include derivatized tyrosine and serine residues. The reactions in this section employ catalyst 2 (Cl$_2$(PCy$_3$)$_2$Ru=CHPh) as the RCM catalyst but in other respects the reaction conditions are similar to those employed for Equation 1 (see Experimental Procedures section for exact conditions). Equation 6 shows the RCM of a dityrosine precursor to yield the ring closed product in 70% yield and Equation 7 shows the RCM of a serine-glycine precursor to yield the ring closed product in 56% yield. These reactions demonstrate that the present invention may use precursors other than allyl substituted glycine.

EQUATION 6

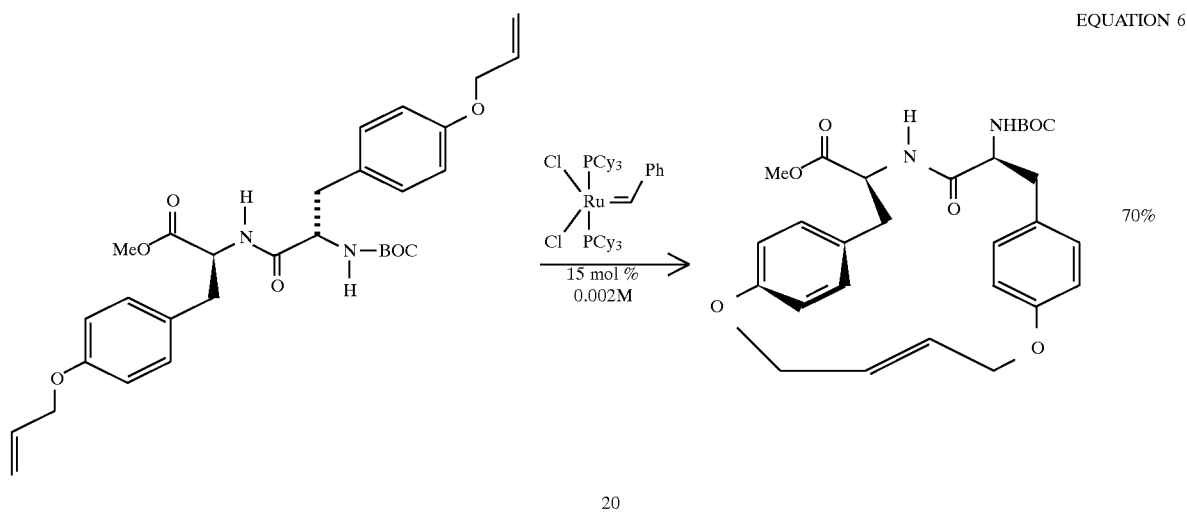

EQUATION 7

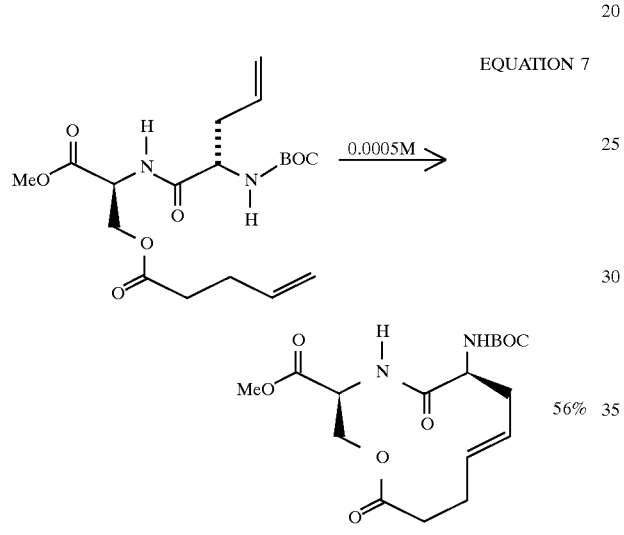

Preparation of a Stabilized β-turn by RCM

This example shows the synthesis of covalently stabilized β-turns using the RCM methodology of the present invention. β-turns are key secondary structural elements in peptides that have been implicated in numerous biological recognition events. β-turns are a structural motif that reverses the direction of a peptide chain and are often found at the surfaces of proteins.

Equation 8 shows a disulfide stabilized β-turn reported by Balaram in Tetrahedron, 40, 2577 (1984), and the analogous tetrapeptide olefin that we attempted to prepare.

EQUATION 8

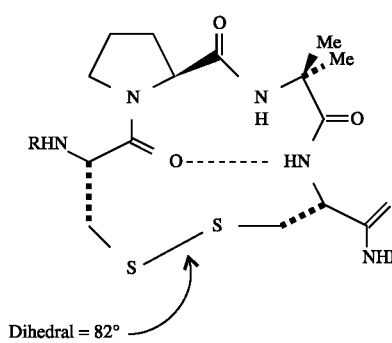

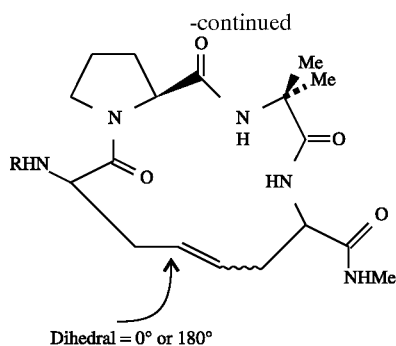

In our initial study of this system, we prepared a statistical mixture of the four stereoisomer of the tetrapeptide precursor 17.

EQUATION 9

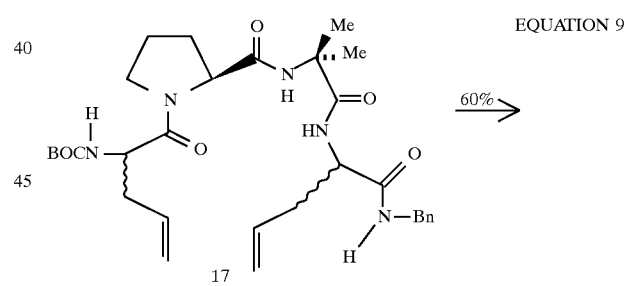

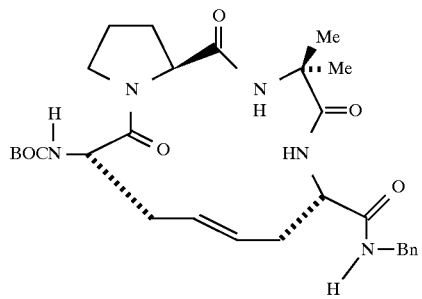

Treatment of a mixture of the four diastereomers with catalyst 1 (20 mol %, 0.002M, 40° C.), yielded the single macrocycle diastereomer 16 shown in Equation 9. The majority of the reaction mixture comprised of unreacted precursor. Independent synthesis of the (R,S,R) and (S,S,S) acyclic tetrapeptide precursors was then accomplished.

When the (S,S,S)-tetrapeptide precursor was subjected to the reaction conditions (S,S,S)-16 was obtained in 60% yield, and the product was identical to that obtained from the analogous experiment on the mixture. In contrast, under the same conditions the (R,S,R)-acyclic tetrapeptide precursor was recovered unchanged.

To explore the scope of the tetrapeptide ring-closing reaction, we prepared additional tetrapeptide precursors where we systematically replaced the conformationally constrained amino acids proline (Pro) and aminoisobutyric acid (Aib) in peptide precursor 17. The Pro-Aib sequence is known to restrict the conformational space of peptides; therefore, we examined substrates where these amino acids were replaced with less rigidifying residues.

Replacement of the Aib residue with protected tyrosine gives peptide precursor 20 (Equation 10). The Pro-Tyr dipeptide sequence is that which spans the cysteine residues in the glutaredoxin active site. Compound 20 therefore represented an attempt to synthesize a carbon-carbon bond mimic of the active site of this protein. Equation 10 shows the RCM cyclyzation of peptide precursor 20. Exposure of 20 to the ruthenium catalyst 2 under our standard macrocyclization conditions (0.004M, $CH_2Cl_2$, 40° C.) resulted in clean formation of the macrocycle 21 in 80% yield. This demonstrates that two consecutive conformationally constrained amino acids are not required for the synthesis of tetrapeptide macrocycles (β-turn mimetics) by RCM.

EQUATION 10

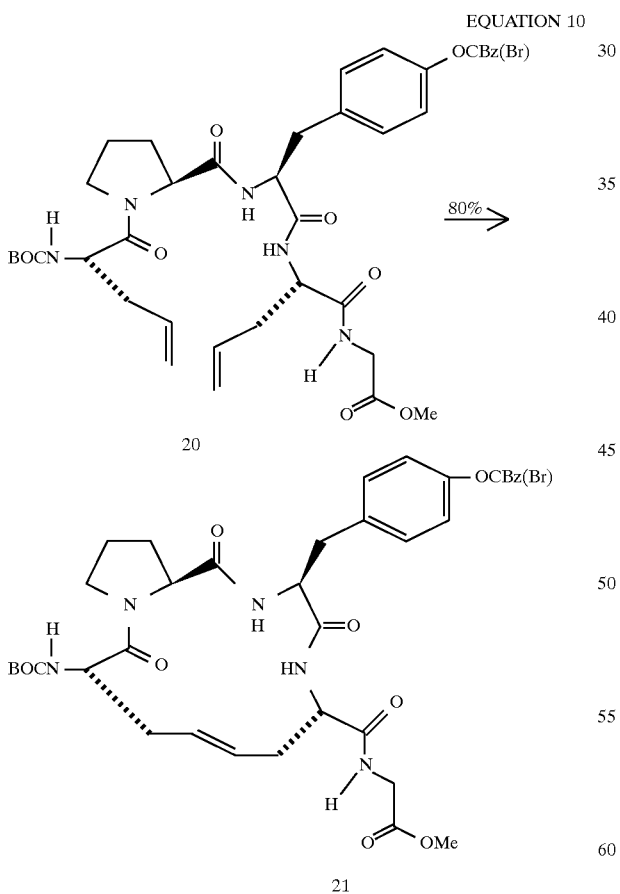

Replacement of both the proline and the Aib residues in precursor 17 with leucines gives peptide precursor 22 (Equation 11), which is devoid of conformationally restricted amino acids in the bridging positions. Equation 11 shows the RCM cyclization of peptide precursor 22. Once again, exposure to the catalyst 2 resulted in very efficient macrocyclization to afford cyclic tetrapeptide 23 in 60% yield.

EQUATION 11

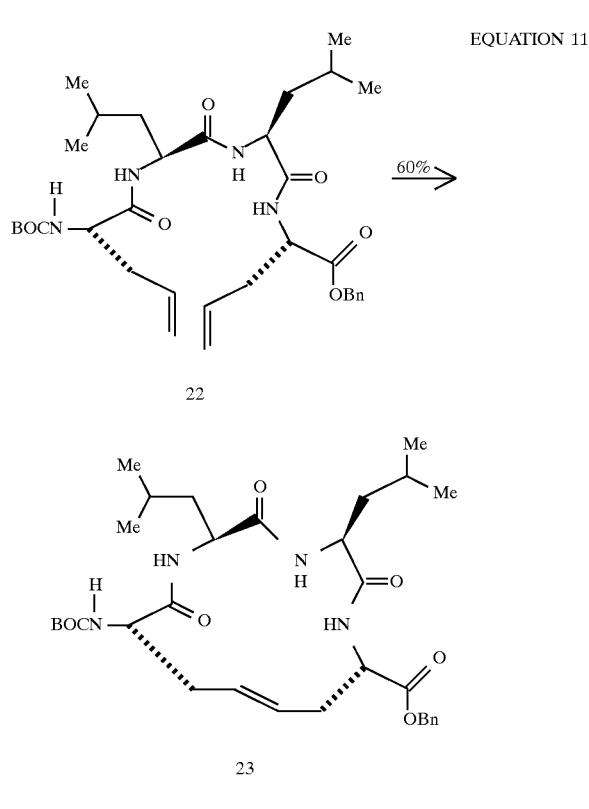

Synthesis of Peptidomimetics Including Saturated Cross-Links

In addition to yielding a product which contains a C—C double bonded cross-link, the present invention can also yield products containing an unsaturated cross-link. Equation 12 shows the RCM of precursor 13 to yield product 14. This first step is carried out using catalyst 2 and under the reaction conditions used for Equation 9. Subsequent hydrogenation of the unsaturated ring-closed product 14 yields the unsaturated product in quantitative yield.

The hydrogenation reaction conditions are as follows. The unsaturated macrocyclic peptide 14 is dissolved in ethanol and 10% Pd/C catalyst is added. An atmosphere of hydrogen is then introduced and the mixture is allowed to sit for 2 hours. The hydrogen is then purged with Argon, and the mixture is filtered to remove the catalyst and concentrated to afford the saturated macrocyclic peptide.

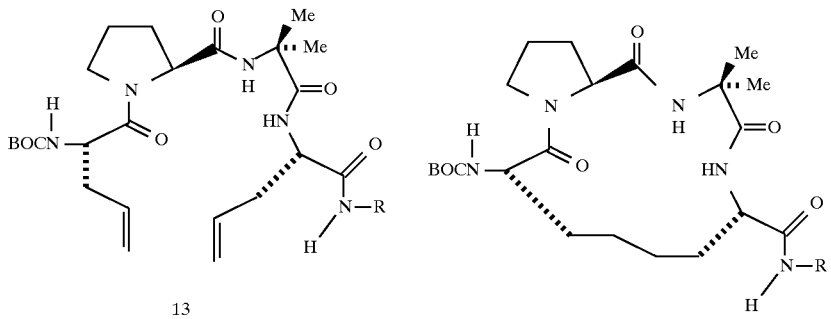

EQUATION 12

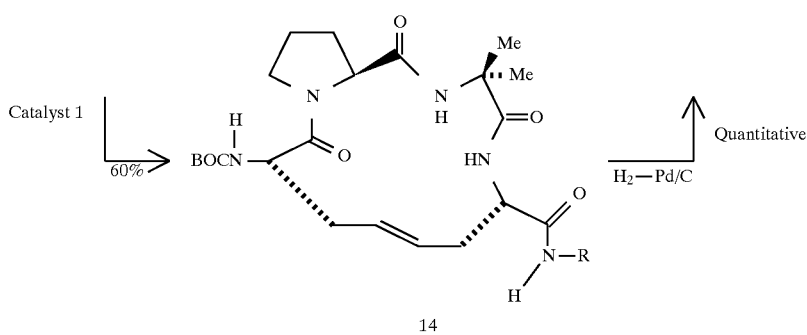

RCM Using Solid-Support Bound Peptides

The RCM reactions of the present invention may be carried out using solid-support bound peptide techniques, which are also known as SPPS or Solid-Phase-Peptide-Synthesis techniques. In these techniques one end of the peptide precursor is anchored to an insoluble solid support such as a polymeric resin or glass bead. The required reactions are then carried out and the product is subsequently cleaved from the solid support. For a detailed description of these techniques see for example, Synthetic Peptides, Edited by Gregory A. Grant, W. H. Freeman & Co. 1992, which is incorporated herein by reference.

SPPS techniques are especially useful when the RCM precursors are larger peptide structures. The reaction conditions for RCM of solid-support bound peptides are similar to those used in the solution based reactions described above. Interestingly, attaching the peptide precursor to a solid support presents no reactivity problems, and in certain cases enhances results.

Equation 13 shows an example of the experimental procedure for carrying out the present invention using SPPS techniques. First, the peptide precursor containing the allylglycine residues [Val-Xaa-Tyr-Pro-Xaa-Gly-(SEQ ID NO:1)] is synthesized in linear fashion using conventional Fmoc SPPS techniques, in which the solid support is based on Polyethyleneglycol/Polystyrene resins ("PEG/PS"), 0.1–0.2 mol/gram.

The beads are swelled in dichloromethane and catalyst 2 is added. The temperature of the mixture is maintained between about 25° C. and about 45° C. and the mixture is stirred for approximately 24 hours. The solution is then drained and the beads subjected to standard cleavage conditions. The cyclic products may then be isolated by standard chromatographic techniques. Equation 13 shows the synthesis of a conformationally restricted -val-gly-tyr-gly-gly-(SEQ ID NO:2) peptide using SPPS techniques, which affords the product in 65% yield.

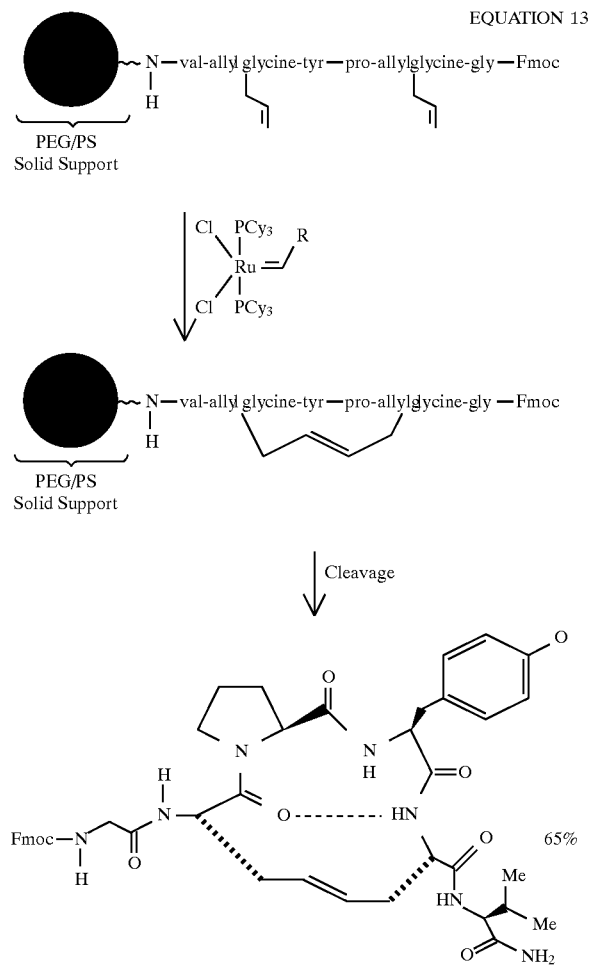

EQUATION 13

Synthesis of Covalently Stabilized RGD peptide by RCM using Solid-Phase-Peptide-Synthesis Techniques This example shows the synthesis of a covalently stabilized cyclic RGD peptide using the SPPS methodology of the present invention. The RGD (-Arginine-Glycine-Aspartic acid-) motif is well known in cell adhesion biochemistry as a highly potent inhibitor of platelet aggregation. There is extensive research in the development of small RGD containing peptides and their mimetics as antithrombic agents. Moreover, cyclic RGD peptides have, in several cases, shown markedly higher activity than their linear counterparts. See for example the review article by Ojima et al titled "Antithrombic Agents: From RGD to Peptide Mimetics" Bioorganic and Medicinal Chemistry, Vol 4, pp 337–360, 1995.

Equation 14 shows the SPPS of conformationally restricted RGD product [-Gly-Xaa-Xaa-Gly-Xaa-Xaa-(SEQ ID NO:3] using the RCM methods of the present invention. Treatment of the solid support bound precursor using catalyst 1 and the reaction conditions described for Equation 1 followed by cleavage from the solid support yielded the RGD product in 50% yield. After undergoing the RCM reaction and solid support cleavage, the protecting groups in the conformationally restricted product can be cleaved by conventional methods yielding the active cyclic RGD peptide fragment.

Experimental Procedures
General Analytic Procedures.

NMR spectra were recorded on a General Electric QE-300 or Bruker AM-500 spectrometer, Chemical shifts are reported in parts per million (ppm) downfield from tetramethylsilane (TMS) with reference to internal solvent. Multiplicities are abbreviated as follows: singlet (s), doublet (d), triplet (t), quartet (q), and multiplet (m). The olefin configurations for tetrapeptides 16, 21, 23, and the product of Equation 7 were assigned by sequential irradiation of the $C_\beta$-protons and analysis of the resulting patterns. The notation d(m) refers to the value of the primary J value extracted from this analysis. Infrared spectra were obtained on a Perkin-Elmer 1600 Series FT-IR. Optical rotations were recorded on a Jasco DIP-181 digital polarimeter at 589 nm and are reported at [α], (concentration in grams/100 mL solvent). Low and high resolution mass spectra were provided by either the Chemistry and Biology Mass Spectrometry Facility (Caltech) or the Southern California Mass Spectrometry Facility (University of California, Riverside).

Analytical thin-layer chromatography (TLC) was performed using Silica Gel 60 F254 precoated plates (0.25 mm thickness) with a fluorescent indicator. Flash column chromatography was performed using Silica Gel 60 (230–400 mesh) from EM Science.

General Peptide Synthesis Procedures.

Peptide precursors 13, 17, 20, and 22 were synthesized by standard solution-phase peptide coupling protocols, using N,N-dicyclohexylcarbodiimide (DCC)/1-hydroxybenzotriazole (HOBT) as peptide coupling agent (see M. Bordansky, Peptide Chemistry, Springer Verlag, N.Y., 1988, pp55–146 and references therein) The synthesis of other precursors is described below.

All RCM reactions were carried out under an argon atmosphere with dry, degassed solvents under anhydrous conditions.

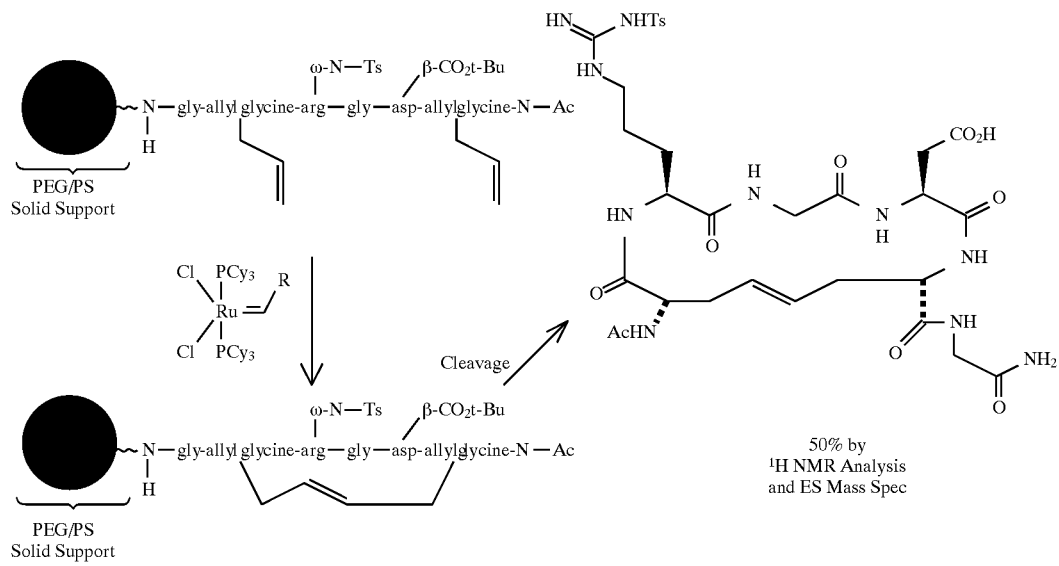

50% by
$^1$H NMR Analysis
and ES Mass Spec

EQUATION 1
Preparation of precursor 2

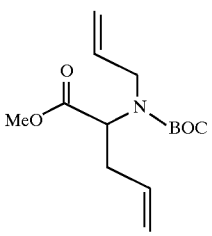

To a 0° C. solution of (+/−)-N—BOC-allylglycine methyl ester (1.4 g, 6.1 mmol) in 30 mL of DMF was added allyl bromide (581 μL, 6.7 mmol) followed by sodium hydride (160 mg, 6.7 mmol). Gas evolution was observed, and the reaction mixture assumed a pale yellow color. The solution was stirred for 1.5 h at 0° C. and 30 min at 25° C. before it was quenched by addition of 20 mL of dilute aqueous NH$_4$Cl. The product was extracted with three 20 mL portions of Et$_2$O, dried over MgSO$_4$ and purified by flash chromatography (1.5 cm×12 cm of silica gel, 20% EtOAc/hexanes) to afford 900 mg (55%) of 2 as a colorless oil.

TLC R$_f$ 0.50 (30% EtOAc/hexane); $^1$H NMR (CDCl$_3$, 500 MHz, not coalesced) δ 5.77–5.60 (br m. 2H), 5,10–4.95 (br m, 4H), 4.5–3.6 (br m, 3H), 3.65 (s, 3H), 2.80–2.65 (br m, 1H), 2,60–2.45 (br m, 1H); $^{13}$C NMR (CDCl$_3$, 125 MHz, not coalesced) δ 171.7, 155.4, 154.6, 135.0, 134.5, 134.4, 134.2, 120.4, 117.6, 117.3, 116.1, 80.5, 80.4, 59.0, 58.2, 51.9, 50.5. 49.0, 34.7, 33.8, 28.2; IR (neat, cm$^{-1}$) 3079, 2978, 1745, 1697, 1643, 1453; HRMS calcd for C$_{14}$H$_{24}$N$_1$O$_4$ (MH+) 270.1705, found 270.1698.

RCM Reaction Conditions

To a 25° C. solution of precursor 2 (170 mg, 0.636 mmol) in 7 ml of C$_6$H$_6$ was added ruthenium catalyst 1 (29 mg, 0.032 mmol, 5 mol %). The orange-brown solution was stirred at this temperature for 2 h before it was concentrated and applied directly to a silica get column. Chromatography (1.5 cm×12 cm silica gel; solvent gradient: 5% EtOAc/Hexane to 20% EtOAc/hexane) afforded 139 mg (91%) of 5 as a clear oil.

TLC R$_f$ 0.40 (30% EtOAc/hexane); $^1$H NMR (CDCl$_3$, 300 MHz, not coalesced) δ 5.77–5.65 (br m, 1H), 5.01–4.80 (br m, 1H), 4.20–3.70 (br m, 2H), 3.71, 3.70 (2 x s, 3H), 2.65–2.50 (br m, 2H), 1.49, 1.46 (2 x s, 9H); $^{13}$C NMR (CDCl$_3$, 75 MHz, not coalesced) δ 172.3, 155.9, 124.5, 124.2, 122.4, 122.0. 80.4, 52.4, 52.3, 51.0, 42.3, 41.6, 28.4, 26.7, 26.6; IR (neat,cm$^{-1}$) 2976, 1746, 1694, 1454, 1403; HRMS calcd for C$_{12}$H$_{18}$N$_1$O$_4$ (M-H) 240.1236, found 240.1236.

EQUATION 2

Preparation of precursor 3

To a solution of N-allyl-N-BOC-glycine methyl ester (1.17 g, 5.10 mmol) in 20 mL of CH$_2$Cl$_2$ was added 10 mL of TFA. The mixture was stirred for 1 h before it was concentrated and, redissolved in 25 mL of CH$_2$Cl$_2$. The solution was washed with 100 mL of saturated NaHCO$_3$ solution, dried over Na$_2$SO$_4$, filtered and concentrated. The unpurified amino was then dissolved in 15 mL CH$_2$Cl$_2$ and treated with (+/−)-N-BOC-allylglycine (400 mg, 1.86 mmol), DCC (383 mg, 1.86 mmol) and DMAP (25 mg, 0.121 mmol). The mixture was stirred for 1 h as a white precipitate formed. The mixture was filtered, concentrated and chromatographed (1.5 cm×10 cm silica gel, 20% EtOAc/Hexanes to 50% EtOAc/hexane) to afford 566 mg (93%) of 3 as a clear oil.

TLC R$_f$ 0.40 (30% EtOAc/hexane); $^1$H NMR (CDCl$_3$, 500 MHz, not coalesced) δ 5.81–5.70 (m, 2H), 5.29–5.04 (m, 5H), 4.65 and 4.40 (q, J=8.2 Hz, 1H), 4.21 (d, J=7.2 Hz, 1H), 4.05–3.80 (m, 3H), 3.82 (d, J=7.2 Hz, 1H), 3.71 and 3.68 (2 x s, 3H), 2.50–2.40 (m, 1H), 2.34–2.30 (m, 1H), 1.38 and 1.37 (2 x s, 9H); $^{13}$C NMR (CDCl$_3$), 125 MHz, not coalesced) δ 172.3, 172.1, 169.5, 169.3, 155.2, 155.0, 132.9, 132.6, 132.2, 118.5, 118.4, 118.1, 79.6, 79.5, 52.3, 52.0. 51.2, 49.9, 49.7, 49.4, 48.2, 46.9, 37.6, 37.3, 28.2 28.1; IR (neat, cm$^{-1}$) 3320, 2979, 1747, 1713, 1650, 1514, 1454; HRMS calcd for C$_{16}$H$_{27}$N$_2$O$_5$ (MH+) 327.1920, found 327.1914.

RCM Reaction Conditions

To a 50° C. solution of peptide precursor 3 (160 mg, 0.491 mmol) in 60 ml of CHCl$_3$ was added ruthenium catalyst 1 (29 mg, 0.032 mmol, 5 mol %). The orange-brown solution was stirred at this temperature for 4 h before it was concentrated and applied directly to a silica gel column. Chromatography (1.5 cm×12 cm silica gel; 25% EtOAc/Hexane) afforded 76 mg (52%) of 6 as a clear oil.

TLC R$_f$ 0.15 (30% EtOAc/hexane); $^1$H NMR (CDCl$_3$, 500 MHz) δ 5.76–5.68 (m, 2), 4.91 (m, 1H), 4.52 (br d, J=17 Hz, 1H), 4.35 (d, J=17.4 Hz, 1H), 4.03 (d, J=17.4 Hz, 1H), 3.70 (s, 3H), 3.70 (m, 1H), 3.32 (dd, 1=17.6, 7.2 Hz, 1H), 2.63 (dd, J=18.1, 4.1 Hz, 1H), 2.23 (m, 1H), $^{13}$C NMR (CDCl$_3$, 125 MHz) δ 172.9, 169.4, 154.9, 129.9, 123.6, 79.5, 52.2, 50.1, 50.0, 47.3, 33,2, 28.3; IR (neat, CM$^{-1}$) 3272, 2973, 1759, 1715, 1650, 1538, 1487, 1454; HRMS calcd for C$_{14}$H$_{23}$N$_2$O$_5$ (MH+) 299.1607, found 299.1603.

EQUATION 3
Preparation of precursor 4

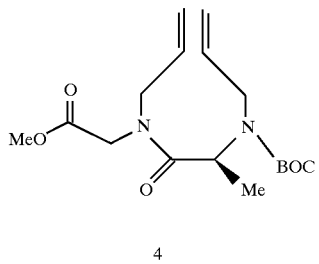

4

To a −78° C. solution of N—BOC-ala-gly-methyl ester (180 mg, 0.66 mmol) in 5 mL of THF was added allyl bromide, (125 μL, 1.45 mmol) followed by phosphazene-P4 base (968 μL. 1.38 mmol). The mixture war stirred at −78° C. for 1 h and then warmed to 25° C. for 30 min. The reaction mixture was concentrated and purified by chromatography (1–5 cm×12 cm silica get, 25% EtOAc/Hexane) to afford 44 mg (20%) of 4 as a colorless oil.

TLC $R_f$ 0.55 (50% EtOAc/hexane); $^1$H NMR (toluene $d_8$, 125 MHz, 80° C.—not fully coalesced) δ 5.8 (br m, 1H), 5.65 (br m 1H) 5.30–4.80 (m, 5H), 4.20–3.70 (m, 6H), 3.40 (s, 3H), 1.40 (s, 9H), 1.28 (d, 3H, J=6.8 Hz); $^{13}$C NMR (toluene d-8, 125 MHz, 80° C., not fully coalesced) δ 172.0, 169.7, 155.8, 136.9, 134.1, 117.3, 115.7, 80.1, 51.4, 47.6, 46.5, 28,6, 16.4; IR (neat, cm−1) 2980, 1754, 1660, 11450; HRMS cold for $C_{17}H_{29}N_2O_5$ (MH+) 341.2076, found 341.2064.

RCM Reaction Conditions

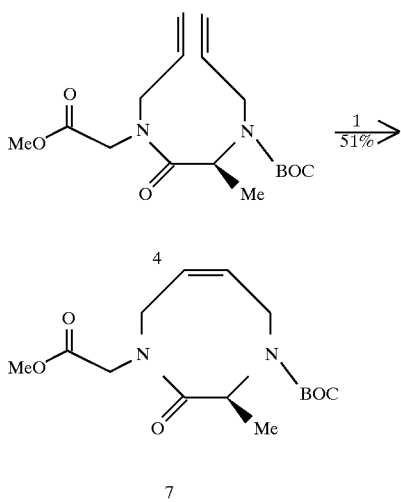

To a 50° C. solution of peptide precursor 4 (17 mg, 0.050 mmol) in 5 ml of $C_6H_6$ was added ruthenium catalyst I (7 mg, 0.008 mmol, 16 mol %) as a solution in 5 mL of $C_6H_6$. The orange-brown solution was stirred at this temperature for 24 h before it was concentrated and applied directly to a silica gel column. Chromatography (1.5 cm×12 cm silica gel; 25% EtOAc/Hexane) afforded 8 mg (51%) of 7 as a clear oil.

TLC $R_f$ 0.30 (50% EtOAc/hexane), $^1$H NMR (toluene $d_8$, 300 MHz, 80° C. not fully coalesced) δ 5.60 (m, 1H), 5.37 (m, 1H), 5.00 (bm, 1H), 4.40–3.00 (br m, 6H), 3.35 (s, 3H), 1.40 (br d, J=7 Hz), 1.38 (s, 9H); $^{13}$C NMR ($C_6D_6$, 125 MHz, 70° C.—not fully coalesced) δ 171.2, 169.3, 154.3, 134.4 (br), 175.2 (br), 79.9, 51.2, 49.9, 45.4, 43.2 (br), 30.0. 28.4. 17.1; IR(neat,cm$^{-1}$) 2926, 1755, 1693, 1659, 1436, 1393; HRMS calcd for $C_{15}H_{24}O_5N_2$(M+) 312.1685, found 312.1678.

EQUATION 6
Preparation of precursor

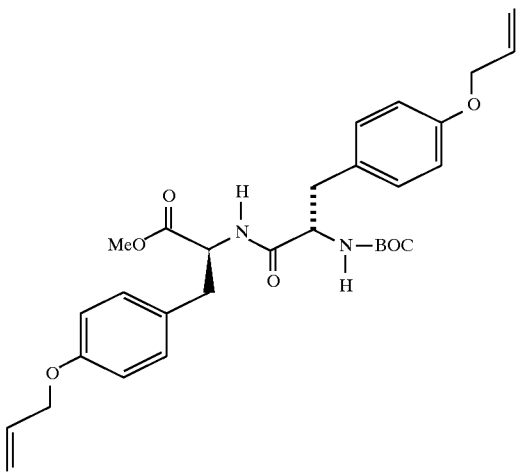

To a solution of N—BOC-dityrosine methyl ester (3.26 g, 7.10 mmol) in 30 mL of acetone was added allyl bromide (1.71 mL, 19.8 mmol) and finely powdered $K_2CO_3$ (2.94 g, 21.3 mmol). The reaction mixture war stirred for 48 h at 25° C. before being filtered through a celite pad. Purification of the residue by chromatography (3 cm×12 cm silica gel, solvent gradient: 20% EtOAc/hexane to 50% EtOAc/hexane) afforded the peptide precursor as a white solid.

TLC $R_f$ 0.50 (50% EtOAc/hexane); $[\alpha]_D$+20.7 (c 2.0, $CH_2Cl_2$); $^1$H NMR ($CDCl_3$, 500 MHz) δ 7.06 (d, J=8.4 Hz, 2H), 6.87 (d, J=8.4 Hz, 2H), 6.79 (d, J=8.4 Hz. 2H), 6.75 (d, J=8.4 Hz, 2H), 6.38 (br d, J=7.5 Hz, 1H), 6.00 (m, 2H), 5.35 (dd, J=17.1, 0.6 Hz, 2H), 5.23 (br d, J=9.3 Hz, 2H), 4.92 (br s, 1H), 4.71 (br d, J=6.2 Hz, 1H), 4.46 (br t, J=4.1 Hz, 4H), 4.29 (br s, 1H), 3.63 (s, 3H), 2.95 (m, 4H), 1.38 (s, 9H); $^{13}$C NMR ($CDCl_3$, 125 MHz) δ 171.3, 170.7, 157.6 (br d), 155.1. 133.2, 130.2, 130.1, 128.6, 127.8, 117.3, 117.2. 114.8, 114.7, 79,9, 68.7, 68.6, 55.8, 53.3, 51.9, 37.3. 37.0, 28.1; IR ($CH_2Cl_2$, cm$^{-1}$) 3420, 2981, 2932, 1742, 1713, 1681, 1610, 1510, 1361; HRMS calcd for $C_{30}H_{39}N_2O_7$ (MH+) 539.2757, found 539.2766.

RCM Reaction Conditions

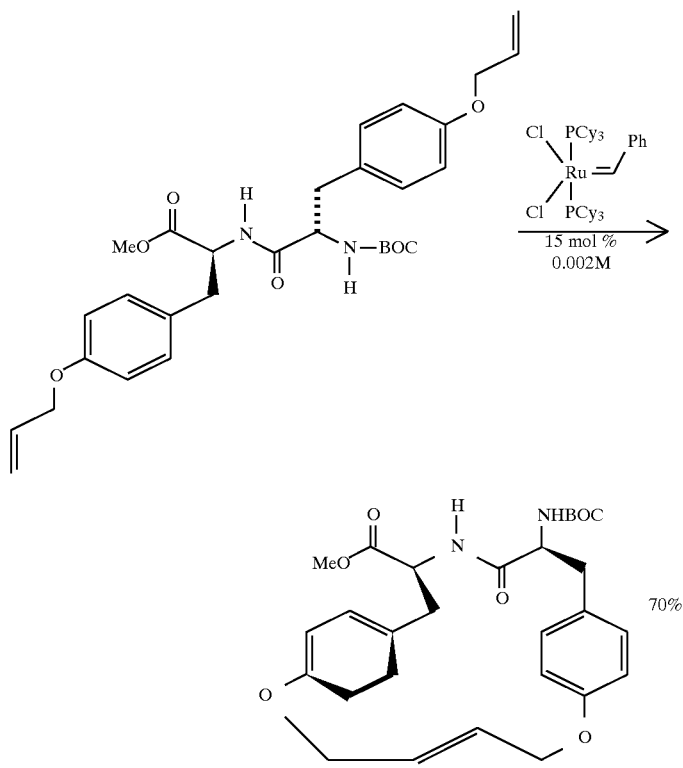

To a 50° C. solution of the peptide precursor (130 mg, 0.0.241 mmol) in 100 ml of CH$_2$Cl$_2$ was added ruthenium catalyst 2 (29 mg, 0.072 mmol). Within 5 min, the purple solution became orange-brown and the solution was stirred for an additional 2.5 h, when TLC analysis showed full disappearance of starting material. Triethylamine (1 mL) was added to the solution to deactivate any remaining active catalyst. The solution was then concentrated to afford an oily brown mixture. Purification by chromatography (3 cm×12 cm silica gel, 50% EtOAc/hexane) afforded 83 mg (68%) of the ring-closed product as a white powder.

Olefin Configuration not assigned: TLC R$_f$ 0.45 (50% EtOAc/hexane); [α]$^D$+46.4 (c 1.0, CH$_2$O$_2$); $^1$H NMR (CDCl$_3$, 500 MHz) δ 7.04 (br s, 2H), 6.77 (br s, 2H), 6.68 (t, J=8.5 Hz, 4H), 5.90 (br m, 1H), 5.83 (s, 2H), 5.25 (br s, 1H), 4.85 (br s, 1H), 4.66 (m, 4H), 4.39 (br t, $^1$H), 3.70 (s, 3H; -minor rotomer at 3.77), 3.34 (br d, J=12.6 H, 1H), 2.98 (br s, 2H), 2.63 (dd, J=14.0, 8.9 Hz, 1H), 1.49 (s, 9H); $^{13}$C NMR (CDCl$_3$, 125 MHz, 25° C.—not fully coalesced) δ 171.2, 171.1. 156.8, 156,6, 155.5, 130.5, 130.2, 130.0, 129.7, 129.5, 129.2, 127.4, 115.6, 115.4, 115.3, 80.9, 67.0, 66.7, 64.7, 64.1, 55.6, 52.7, 52.1, 37.4, 36.2, 28.31 IR (CH$_2$Cl$_2$, cm$^{-1}$) 3683, 3411, 2933, 1744, 1713, 1676, 1611, 1511, 1484; HRMS calcd for C$_{28}$H$_{35}$N$_2$O$_7$ (MH+) 511.2444, found 511.2437.

EQUATION 7
Preparation of Peptide Precursor

N—BOC serine methyl ester (1.0 g, 4.56 mmol) was dissolved in 75 mL CH$_2$Cl$_2$ and treated with 4-pentenoic acid (466 μL, 4.56 mmol), DCC (940 mg, 4.56 mmol), and DMAP (100 mg, 0.82 mmol.). A white precipitate formed immediately, and the solution was stirred for 12 h. The mixture was filtered, washed with 50 mL of a 10% citric acid solution, followed by 50 ml saturated NaHCO$_3$ solution. The solution was dried over MgSO$_4$, and concentrated to afford 1.37 g of the crude esterified product as a pale yellow oil with some crystalline domains. To a portion (1.00 g, 3.32 mmol) of the crude product dissolved in 25 mL of CH$_2$Cl$_2$ was added an excess of TFA (7.67 mL, 99.6 mmol). The solution was allowed to stir at room temperature for 2.5 h after which the solution was concentrated to an orange oil and dried under high vacuum. The oil was then taken up in 60 ml of CH$_2$Cl$_2$ and treated with triethylamine (560 μL, 3.98 mmol). After stirring for 15 min, N-BOC-allylglycine (715 mg, 3.32 mmol), HOBT (670 mg, 4.98 mmol), and DCC (690 mg, 3.32 mmol) were added to the solution. A white precipitate formed immediately, and the solution was allowed to stir 9 h. The mixture was then filtered, washed with 75 mL of a 10% citric acid solution, and subsequently washed with 75 ml saturated NaHCO$_3$ solution. The product was dried over MgSO$_4$, and concentrated to yield a yellow oil. Purification by column chromatography (4 cm×15 cm silica gel, solvent gradient 25% EtOAc/hexane to 50% EtOAc/hexane) afforded 556 mg (42%) of the peptide precursor as a clear oil with some crystalline domains.

TLC R$_f$ 0.21 (75% Hexane/EtOAc); [α]$_D$+13.1 (c 1.0, CH$_2$Cl$_2$); $^1$H NMR (CDCl$_3$, 500 MHz) δ 6.92 (br d, J=7 Hz, 1H), 5.81–5.68 (m, 2H,), 5.15–4.97 (m, 5H), 4.80–4.78 (m, 1H), 4.42 (dd, J=1 1, 4 Hz, 1H), 4.36 (dd, J=11, 3 Hz, 1H), 4.17 (m, 1H), 3.73 (s, 3H) 2.54–2.43 (m, 2H), 2.38 (m, 2H), 2.32 (m, 2H), 1.41 (s, 9H); $^{13}$C NMR (CDCl$_3$, 125 MHz) δ 172.6, 171.6, 169.7, 155.6, 136.6, 133.1, 119.2, 115.8, 80.4, 63.8, 52.9, 52.0, 36.8, 34.1, 33.7. 28.8, 28.4; IR (CH$_2$Cl$_2$, cm$^{-1}$) 3680, 3427, 2981, 1746, 1716, 1685, 1494, 1438; HRMS calcd for C$_{19}$H$_{31}$N$_2$O$_7$ (MH+) 399.2131, found 399.2140.

RCM Reaction Conditions

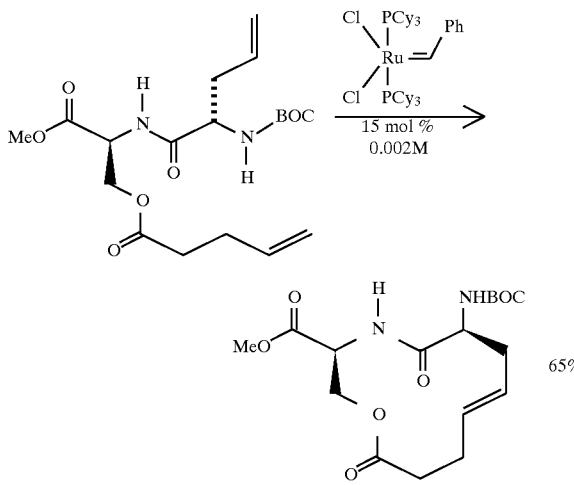

To a solution of the peptide precursor (50 mg, 0.1 25 mmol) in 230 ml of CH$_2$Cl$_2$ was added via syringe a solution of ruthenium catalyst 2 (30 mg, 0.036 mmol) predissolved in 20 ml CH$_2$Cl$_2$. The purple solution was heated to 45° C., and turned orange-brown in color over 20 min. The solution was stirred at 45° C. for 20 h. The solution was then concentrated under reduced pressure to afford an oily brown mixture. Purification by chromatography (3 cm×10 cm silica gel; eluent: (50% EtOAc/hexane) afforded 28 mg (56%) of the ring closed product as an off-white powder.

TLC R$_f$ 0.30 (50% EtOAc/hexane); [α]$_D$+41.1 (c 1.0, CH$_2$Cl$_2$); $^1$H NMR ((CD$_3$)$_2$SO, 500 MHz, 60° C.—not fully coalesced) δ 7.47 (br d, J=8 Hz, 1H), 6.03 (apparent s, 1H), 5.48 (d(m), J=15 Hz, 1H), 5.32 (d(m), J=15 Hz, 1H), 4.72 (m, 1H), 4.52 (apparent t, J=11 Hz, 1H), 4.16 (dd, J=11, 4 Hz, 1H), 4.07 (m, 1H), 3.64 (s, 3H), 2.44–2.18 (m, 6H), 1.41, 1.40 (2 x s, 91H); $^{13}$C NMR ((CD$_3$)2CO, 75 MHz) δ 172.2, 170.5, 169.5, 155.0, 131.7, 126.0, 78.5, 61,0, 55.0, 52.3, 51.9, 50.1, 35.0, 34.0, 28.1; IR (CH$_2$Cl$_2$, cm$^{-1}$) 3691, 3422, 2929, 1736, 1720, 1683, 4517, 1485; HRMS calcd for C$_{17}$H$_{27}$N$_4$O$_7$ (MH+) 371.1818, found 371.1812.

EQUATION 9
Preparation of Peptide Precursor 17

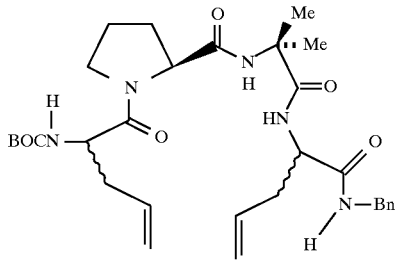

Tetrapeptide precursor 17 was prepared according to the standard solution protocol described in the general experimental procedures above.

TLC R$_f$ 0.45 (100% EtOAc); [α]$_D$–53.0 (c 0.7, CH$_2$Cl$_2$); $^1$H NMR (CD$_3$CN, 500 MHz) δ 7.74 (br t, 1H), 7.29 (m, 5H), 7.22 (m, 1H), 7.0 (br s, 1H), 5.83–5.78 (m, 2H), 5.55 (br d, 1H), 5.18–5.05 (m, 4H), 4.42–4.21 (m, 5H), 3.99 (br t, 1H), 3.76 (m, 1H), 3.60 (m, 1H), 2.75 (m, 1H), 2.5–1.1.7 (m, 8H), 1.40 (s, 12H), 1.35 (s, 3H); $^{13}$C NMR (CD$_3$CN, 125 MHz) δ 175.5, 174.0, 173.5, 172.6, 157.0, 140.9, 136.6, 135.0, 129.7, 128.7, 128.1, 119.3, 11.8.11 80.5, 63.6, 58.3, 54.8, 53.8, 49.0, 43.9. 36.9. 36.6. 30,0, 29.0, 27.6, 26.3, 24.8; IR (CH$_2$O$_2$, cm$^{-1}$) 3425, 33399 2982, 2934, 1668, 1498, 1439; HRMS calcd for C$_{31}$H$_{46}$N$_5$O$_6$ (MH+) 584.3448, found 584.3471.

RCM Reaction Conditions

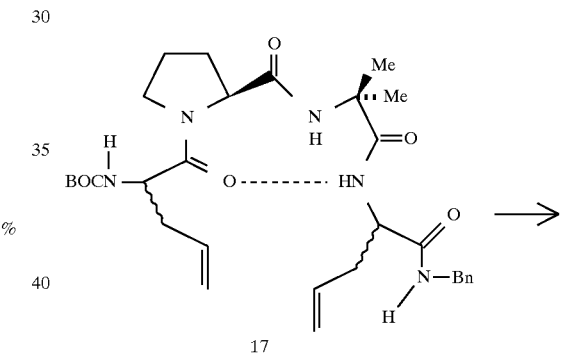

Prepared as a mixture of
4 Diastereomers

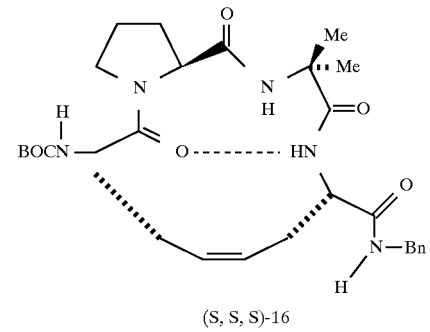

(S, S, S)-16

To a solution of peptide precursor 17 (210 mg, 0.360 mmol) in 80 ml of CH$_2$Cl$_2$ was added via cannula a solution of ruthenium catalyst 1 (67 mg, 0.072 mmol) predissolved in 20 ml CH$_2$Cl$_2$. The orange-brown solution was heated to 40° C. and stirred at this temperature for 20 h. The solution was then concentrated under reduced pressure to afford an oily brown mixture. Purification by chromatography (1.5cm× 15cm silica gel; solvent gradient: 50% EtOAc/hexane to 100% EtOAc) afforded 120 mg (60%) of 16 as an off-white Powder. Macrocycle 16 can be recrystallized by dissolving the powder in $CH_2Cl_2$ and layering the solution with hexanes. White needles and prisms result. However, upon removal of solvent the amorphous white powder is reobtained.

TLC $R_f$ 0.20 (100% EtOAc); $[\alpha]_D$ +63.8 (c 0,73, $CH_2Cl_2$); $^1$H NMR ($CD_2Cl_2$, 500 MHz) δ 7.33–7.21 (m, 5H), 7.01 (br d. J=7.2 Hz, 1H), 6.91 (br t, 1H), 6.53 (br s, 1H), 5.58 (d, J=7.8Hz, 1H), 5.51–5.42 (d(m), J=15 Hz, 1H), 5.39–5.30 (d(m), J=15 Hz, 1H), 4.65–4.59 (m, 2H), 4.50 (q, 1=6 Hz, 1H), 4.29 (dd, J=15, 5.0 Hz, 1H), 4.20 (t, J=7.2 Hz, 1H), 3.69 (m, 1H), 3.58 (m, 1H), 2.6–1.88 (m, 8H), 1.50 (s, 3H), 1.41 (s, 9H), 1.35 (s, 3H); $^{13}$C NMR ($CD_2Cl_2$, 125 MHz) δ 175.4, 172.5, 172.1, 172.0, 155.0, 139.9, 131.0, 129.6, 128.9, 128.5, 1283, 80.5, 62.2, 61.9, 58.4, 53.4, 48.7, 44.2, 34.9, 34.4, 29.3, 29.2, 26.8, 23.9; IR ($CH_2Cl_2$, cm$^{-1}$) 3424, 3324, 3054, 2985, 1691, 1632, 1498, 1444; HRMS calcd for $C_{29}H_{42}N_5O_6$(MH+) 556.3135, found 556.3145.

EQUATION 10
Preparation of Peptide Precursor 20

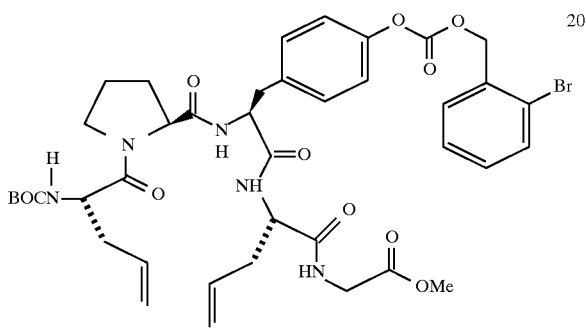

20

Pentapeptide 20 was prepared according to the standard solution protocol described in the general experimental procedures above.

TLC $R_f$ 0.27 (83% EtOAc/hexane); $[\alpha]_D$ –38.0 (c 1.1, $CH_2Cl_2$); $^1$H NMR (($CD_3$)$_2$SO, 500 MHz) δ 8.34 (br t, J=5 Hz, 1H), 7.94 (d, J=8 Hz, 1H), 7.89 (d, J=8 Hz, 1H), 7.71 (d, J=8 Hz, 1H), 7.57 (d, J=8 Hz, 1H), 7.46 (t, J=8 Hz, 1H), 7.36 (t, J=8 Hz, 1H), 7.29 (amide NH obscured, apparent d, J=8 Hz, 3H), 7.13 (d, J=7 Hz, 2H), 6.91 (d, J=8 Hz, 1H), 5.83–5.70 (m. 2H), 5.32 (s. 2H), 5.12–5.01 (m, 4H), 4.48 (br q, J=9 Hz, 1H), 4.40–4.30 (br m, 2H), 4.21 (br q, J=7 Hz, 1H), 3.91–3.80 (m, 2H), 3.63 (s, 3H), 3.60–3.51 (m, 2H), 3.06 (dd, J=14, 4 Hz, 1H), 2.87 (dd, J=14, 9 Hz, 1H), 2.40 (m, 1H), 2,33 (m, 2H), 2.22 (m, 1H), 1.95 (m, 1H), 1.82–1.71 (br m, 3H), 1.36 (s, 9H); $^{13}$C NMR (CDCl$_3$, 125 MHz, not coalesced) δ 172.1, 172.0, 171.4, 170.9, 170.3, 155.6, 153.3, 150.2, 134.8. 134.4, 133.3, 127.7, 123.5, 120.0, 118.9, 118.5, 79.8, 69.6, 63.0, 60.7, 55.9, 52.9, 52.2, 47.6, 41.3, 36.9, 36.5. 28.7, 28.4, 25.2; IR ($CH_2O_2$, cm$^{-1}$) 3415, 3333, 2913, 2851, 1759, 1672, 1605, 1503, 1441, 1364; HRMS calcd for $C_{40}H_{51}N_5O_{11}Br$ (MH+) 856.2768, found 856.2794.

RCM Reaction Conditions

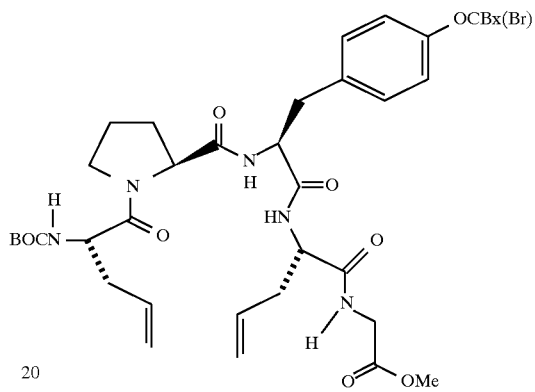

20

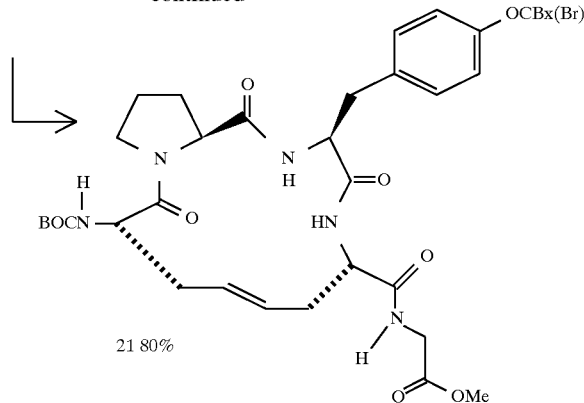

21 80%

To a solution of peptide precursor 20 (200 mg, 0.234 mmol) in 53 ml of $CH_2Cl_2$ was added via syringe a solution of ruthenium catalyst 2 (58 mg, 0.072 mmol) predissolved in 10 ml $CH_2Cl_2$. The purple solution was heated to 45° C. and turned orange-brown in color over a 30 min period. The solution was stirred at 45° C. for 23 h. The solution was then concentrated under reduced pressure to afford an oily brown mixture. Purification by chromatography (3 cm×15 cm silica gel; solvent gradient: 80% EtOAc/hexane to 100% EtOAc) afforded 155 mg (80%) of 21 as an off-white powder.

TLC $R_f$ 0.21 (83% EtOAc/hexane); $[\alpha]_D$ −29.0 (c 1.1, $CH_2Cl_2$), $^1H$ NMR $((CD_3)_2SO$, 500 MHz) & 8.22 (br t, J=6 Hz, 1H), 7.88 (br d, J=9 Hz, 1H), 7.71 (d, J=8 Hz, 1H), 7.57 (d, 1=7 Hz, 1H), 7.46 (t, J=7 Hz, 1H), 7.36 (t, J=7 Hz, 2H), 7.22 (d, J=8 Hz. 2H), 7.13 (amide NH occurred, apparent d, J=8 Hz, 3H), 6.69 (d, J=9 Hz, 1H), 5,46 (d(m), J=15 Hz, 1H), 5.36 (d(m), J=15 Hz, 1H), 5.31 (s, 2H), 4.58 (m, 2H), 4.47 (m, 1H), 3.97 (m, 1H), 3.85 (m, 2H), 3.68 (m, 1H), 3.64 (s, 3H), 3.36 (m, 2H), 2.80 (m, 1H), 2.46 (m, 2H), 2.11 (in, 2H), 1.84 (m, 1H), 1.71 (m, 2H), 1.37 (s. 9H), 1.23 (m, 1H); $^{13}C$ NMR $((CD_3)_2SO$, 75 MHz) δ 171.8, 170.8, 170.2, 170.0, 168.9, 155.0. 152.7, 149.1, 136.5, 134.0, 132.7, 130.7, 130.6, 130.3, 130.1, 128.0, 127.4, 122.9, 120.5, 78.2, 69.2, 60.8. 53.1, 51.7, 51.2, 50.7, 46.5, 35.3, 34.8, 28.5, 28.0, 24.4; IR ($CH_2Cl_2$, $cm^{-1}$) 3426, 3354, 2954, 2923, 2851, 1759, 1687, 1621, 1508, 1446, 1369. 1164; HRMS calcd for $C_{38}H_{47}N_5O_{11}Br$ (MH+) 828.2443, found 828.2455.

EQUATION 11
Preparation of Peptide Precursor 22

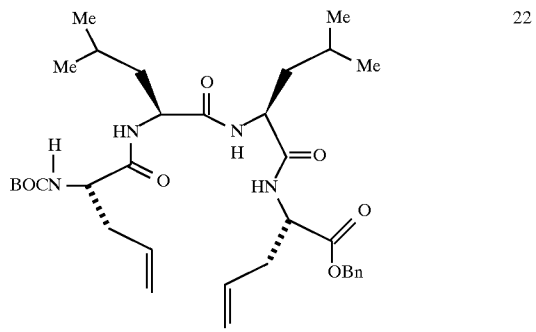

Tetrapeptide 22 was prepared according to the standard solution protocol described in the general experimental above.

TLC $R_f$ 0.41 (80% $CH_2Cl_2$/EtOAc); $[\alpha]_D$ −29.5 (c 1.2, $CH_2Cl_2$); $^1H$ NMR ($CDCl_3$, 500 MHz, not fully coalesced) δ 7.33 (m, 5H), 6.91 (apparent s, 1H), 6.73 (apparent s, 1H), 6.64 (d, J=7 Hz, 1H), 5.74–5.63 (m, 2H), 5.19–5.02 (m, 6H), 4.66 (q, J=7 Hz, 1H), 4.49 (q, J=9 Hz, 1H), 4.39 (q, J=8 Hz, 1H), 4.11 (m, 1H), 2.61–2.38 (m, 4H), 1.73–1.46 (m, 6H), 1.43 (s. 9H), 0.96–0.86 (m, 12H); $^{13}C$ NMR ($CDCl_3$, 125 MHz, not fully coalesced) d 171.9, 171.8, 171.4, 135.7, 133.1, 132.6, 128.8, 128.6, 129.5, 80.7, 67.2, 52.3, 51.9, 41.3, 41.1, 36.8, 36.5, 34.2, 29.9, 28.5, 25.9, 25.1, 25.0, 24,9, 23.2, 23.0, 22,2. 22.1; IR ($CH_2Cl_2$, $cm_{-1}$) 3414, 3339, 2961, 2929, 1740, 1694, 1505, 1456, 1365, 1169; HRMS calcd for $C_{34}H_{53}N_4O_7$ (MH+) 629.3914, found 629.3914.

RCM Reaction Conditions

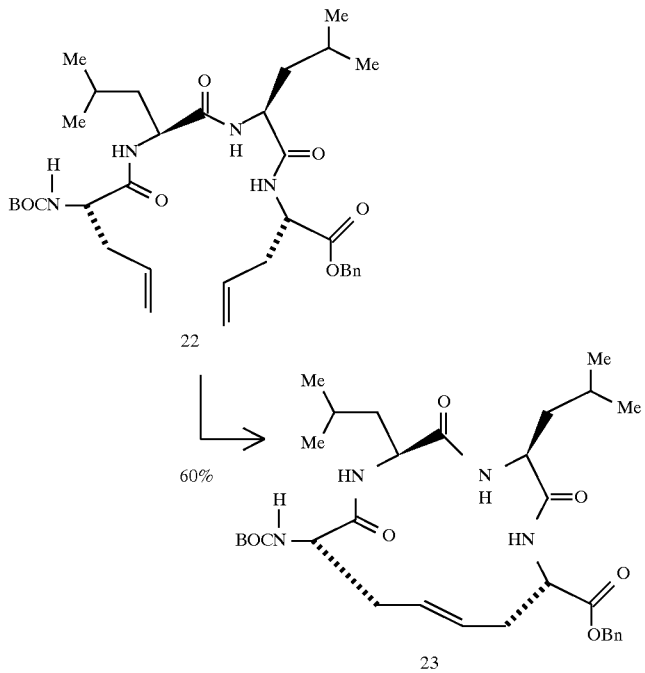

To a solution of peptide precursor 22 (285 mg, 0.453 mmol) in 100 ml of $CH_2Cl_2$ was added via syringe a solution of ruthenium catalyst 2 (112 mg, 0.136 mmol) predissolved in 22 ml $CH_2Cl_2$. The purple solution was heated to 45° C., and turned orange-brown in color over 20 min. The solution was stirred at 45° C. for 21 h. The solution was then concentrated under reduced pressure to afford an oily brown mixture. Purification by chromatography (3 cm×15 cm silica gel; eluent: 80% $CH_2O_2$/EtOAc) afforded 163 mg (60%) of 23 as an off-white powder.

TLC $R_f$ 0.24 (80% $CH_2Cl_2$/EtOAc)- $[\alpha]_D$ −114.0 (c 1.0, $CH_2Cl_2$); $^1H$ NMR ($(CD_3)_2SO$, 500 MHz) δ 7.90 (d, J=9, 1H), 7.80 (d, J=8, 1H), 7.37 (m, 5H), 7.24 (d, 8 Hz, 1H), 5.46 (d(m), J=15 Hz, 1H), 5.16 (d(m), J=15 Hz, 1H), 5.13 (s, 2H), 4.48 (m, 1H), 4,21 (m, 2H), 4.03 (m, 1H), 2.45–2.12 (br m, 4H), 1.66–1.45 (m, 6H), 1.38 (s, 9H), 0.87 (apparent d, J=6 Hz, 6H), 0.81 (apparent t, J=6 Hz, 6H); $^{13}C$ NMR (($CD_3$)$_2CO$, 75 MHz) a 171.9, 170.8, 170.6, 130.3, 128.1, 127.7, 127.6, 127.5, 78.7, 66.0, 53.4, 52.8, 50.6, 50.0, 40.2, 39.7, 34.6, 33.7. 24.4, 24.2, 24.1, 22.5, 22.2, 20.4, 20.3; IR ($CH_2Cl_2$, $cm_{-1}$) 3419, 3339, 2958, 2929, 1740, 1671, 1602, 1515, 1365, 1158; HRMS calcd for $C_{32}H_{49}N_4O_7$ (MH+) 601.3601, found 601.3610.

EQUATION 14
Preparation of Peptide Precursor

The solid supported peptide precursor was prepared by manual solid-phase peptide synthesis. Fmoc-Pal-PEG-PS resin (substitution 0.20 mmol/g) was used to afford C-terminal primary amides. Commercially available reagents and starting materials were purchased from Sigma Chemical Co. Applied Biosystems, Peptides International, and PerSeptive Biosystems. $N^\alpha$-fluorenylmethyloxycarbonyl (Fmoc) protection was employed for all amino acids in the solid-phase synthesis, with the Tyrosine phenol protected as a tert-butylester. Each amino acid was coupled sequentially to the peptide chain grown from the C-terminal amino acid using N,N-diisopropylcarbodiimide 1-hydroxybenzotriazole. A complete coupling in each step was monitored by a quantitative Ninhydrin test. Unreacted N-termini were acetylated using an acetic anhydride/HOBT/diisoprolpylethylamine capping protocol. Fmoc groups were cleaved with 20% piperidine in dimethylformamide (DMF). The peptides were deprotected and cleaved form the resin by treatment with a solution of trifluoroacetic acid(TFA)/anisole/thioanisole (90:5:5) for 2 h.

RCM Reaction Conditions

To a suspension of solid-support bound peptide (300 mg resin, 0.06 mmol theoretical bound peptide) in 22 ml $CH_2Cl_2$ was added via syringe a solution of ruthenium catalyst 2 (25 mg, 0.030 mmol) predissolved in 5 ml $CH_2Cl_2$. The solution turned from pink to orange-brown over 3 h. The suspension was heated to 40° C. and gently stirred for 22 h. The beads were then filtered, rinsed with $CH_2Cl_2$, DMF, and MeOH, respectively and dried under high vacuum. To 270 mg dried resin was added 3 ml of a solution of TFA/anisole/thioanisole (90:5:5). The suspension was shaken gently at room temperature for 2 h, after which the beads were filtered and rinsed with a minimal amount of TFA. The filtrate was reduced in volume to −0.5 ml to yield a brown oil. Trituration with 2:1 ether/hexane afford the crude peptide mixture as an off-white solid. The solid was dissolved in deionized $H_2O$, and freeze-dried to afford a cream powder which was a mixture of 65% ring closed product and 35% peptide precursor.

What is claimed is:

1. A method for synthesizing conformationally restricted peptides by ring closing metathesis, the method comprising the steps of:

(a) synthesizing a peptide precursor containing a first unsaturated C—C bond and a second unsaturated C—C bond; and (b) contacting the peptide precursor with a ring closing metathesis catalyst to yield a conformationally restricted peptide wherein the ring closing metathesis catalyst is a Ruthenium carbene complex catalyst that includes a Ruthenium metal center that is in a +2 oxidation state, has an electron count of 16, and is pentacoordinated.

2. The method according to claim 1, wherein the Ruthenium carbene complex catalyst has the formula

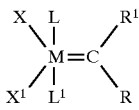

and wherein:

M is Ru;

R and $R^1$ are independently selected from the group consisting of hydrogen, substituted moiety, and unsubstituted moiety wherein the moiety is selected from the group consisting of $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, and the substitution is selected from a group consisting of $C_1$–$C_5$ alkyl, a halide, $C_1$–$C_5$ alkoxy, unsubstituted phenyl, halide substituted phenyl, $C_1$–$C_5$ alkyl substituted phenyl, and $C_1$ -$C_5$ alkoxy substituted phenyl; X and $X^1$ are anionic ligands; and L and $L^1$ are neutral electron donors.

3. The method according to claim 2, wherein L and $L^1$ are phosphines of the formula $PR^3R^4R^5$, wherein $R^3$ is selected from the group consisting of secondary alkyl and cycloalkyl, and $R^4$ and $R^5$ are independently selected from aryl, $C_1$–$Cl_{10}$ primary alkyl, secondary alkyl and cycloalkyl.

4. The method according to claim 3, wherein the catalyst is

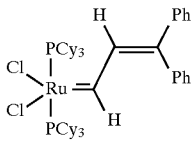

wherein Cy is cyclohexyl or cyclopentyl.

5. The method according to claim 3, wherein the catalyst is

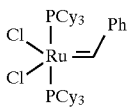

wherein Cy is cyclohexyl or cyclopentyl.

6. The method according to claim 1, wherein the peptide precursor includes one or more functional groups selected from the group consisting of alcohol, thiol, ketone, aldehyde, ester, ether, amine, amide, imine, nitro acid, carboxylic acid, disulfide, carbonate, carboalkoxy acid, isocyanate, carbodiimide, carboalkoxy, and halogen.

7. The method according to claim 1, wherein the first and second unsaturated C—C bonds are olefinic bonds.

8. The method according to claim 7, wherein the peptide precursor is substituted with a first alkenyl group containing the first olefinic bond and a second alkenyl group containing the second olefinic bond.

9. The method according to claim 8, wherein the first and second alkenyl groups are allyl groups.

10. The method according to claim 8, wherein the peptide precursor includes first and second amino acids, the first alkenyl group is directly bonded to an α-carbon or an amine nitrogen of the first amino acid, and the second alkenyl group is directly bonded to an α-carbon or an amine nitrogen of the second amino acid.

11. The method according to claim 10, wherein the first amino acid is an N-terminal amino acid and the second amino acid is a C-terminal amino acid.

12. The method according to claim 10, wherein the first and second amino acids are each either glycine or allyl glycine.

13. The method according to claim 1, wherein the peptide precursor is selected from the group consisting of dipeptides, tripeptides, tetrapeptides, and pentapeptides.

14. The method according to claim 1, wherein the peptide precursor is contacted with the catalyst in the presence of a solvent selected from the group consisting of protic solvent, aqueous solvent, organic solvent, and mixtures thereof.

15. The method according to claim 14, wherein the solvent is an organic solvent.

16. The method according to claim 1, further comprising the step of hydrogenating the conformationally restricted peptide.

17. The method according to claim 16, wherein the conformationally restricted peptide is hydrogenated by being contacted with $H_2$ in the presence of a hydrogenation catalyst.

18. The method according to claim 1, wherein the peptide precursor is anchored to a solid support and the method further includes the step of cleaving the conformationally restricted peptide from the solid support.

19. The method according to claim 18, wherein the solid support is a polyethyleneglycol/polystyrene bead.

20. The method according to claim 1, wherein the peptide precursor contains a first amino acid containing the first unsaturated C—C bond and a second amino acid containing the second unsaturated C—C bond and the first and second amino acids are connected via two intervening amino acid residues.

21. The method according to claim 1, wherein the peptide precursor contains a first amino acid containing the first unsaturated C—C bond and a second amino acid containing the second unsaturated C—C bond and the first and second amino acids are connected via the amino acid sequence -Arginine-Glycine-Aspartic acid-.

22. A method for synthesizing conformationally restricted peptides or amino acids by ring closing metathesis, the method comprising:

contacting a peptide or amino acid precursor containing a first unsaturated C—C bond and a second unsaturated C—C bond with a ring closing metathesis catalyst to yield a conformationally restricted peptide or amino acid wherein the ring closing metathesis catalyst is a Ruthenium carbene complex catalyst that includes a Ruthenium metal center that is in a +2 oxidation state, has an electron count of 16, and is pentacoordinated.

23. The method according to claim 22, wherein the Ruthenium carbene complex catalyst has the formula

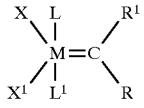

and wherein:

M is Ru;

R and $R^1$ are independently selected from the group consisting of hydrogen, substituted moiety, and unsubstituted moiety wherein the moiety is selected from the group consisting of $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, and the substitution is selected from the group consisting of $C_1$–$C_5$ alkyl, a halide, $C_1$–$C_5$ alkoxy, unsubstituted phenyl, halide substituted phenyl, $C_1$–$C_5$ alkyl substituted phenyl, and $C_1$–$C_5$ alkyl substituted phenyl; X and $X^1$ are anionic ligands; and L and $L^1$ are neutral electron donors.

24. The method according to claim 23, wherein L and $L^1$ are phosphines of the formula $PR^3R^4R^5$, wherein $R^3$ is selected from the group consisting of secondary alkyl and cycloalkyl, and $R^4$ and $R^5$ are independently selected from aryl, $C_1$–$C_{10}$ primary alkyl, secondary alkyl and cycloalkyl.

25. The method according to claim 22, wherein the amino acid precursor includes one or more functional groups selected from the group consisting of alcohol, thiol, ketone, aldehyde, ester, ether, amine, amide, imine, nitro acid, carboxylic acid, disulfide, carbonate, carboalkoxy acid, isocyanate, carbodiimide, carboalkoxy, and halogen.

26. The method according to claim 22, wherein the first and second unsaturated C—C bonds are olefinic bonds.

27. The method according to claim 26, wherein the amino acid precursor is substituted with a first alkenyl group containing the first olefinic bond and a second alkenyl group containing the second olefinic bond.

28. The method according to claim 27, wherein the first and second alkenyl groups are allyl groups.

29. The method according to claim 27, wherein the first alkenyl group is directly bonded to an α-carbon of the amino acid precursor and the second alkenyl group is directly bonded to an amine nitrogen of the amino acid precursor.

30. The method according to claim 22, wherein the amino acid precursor is contacted with the catalyst in the presence of a solvent selected from the group consisting of protic solvent, aqueous solvent, organic solvent, and mixtures thereof.

31. The method according to claim 30, wherein the solvent is an organic solvent.

32. The method according to claim 22, further comprising the step of hydrogenating the conformationally restricted amino acid.

33. The method according to claim 32, wherein the conformationally restricted amino acid is hydrogenated by being contacted with $H_2$ in the presence of a hydrogenation catalyst.

34. The method according to claim 24 wherein X and $X^1$ are both Cl.

35. The method according to claim 24 wherein L and $L^1$ are each of the formula $PCy_3$ wherein Cy is cyclohexyl or cyclopentyl.

36. The method according to claim 24 wherein R is hydrogen and $R^1$ is phenyl.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: YES ( i v ) ANTI-SENSE: NO ( x i ) SEQUENCE DESCRIPTION: SEQ ID NO:1:

Val  Xaa  Tyr  Pro  Xaa  Gly
1                   5

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Val  Gly  Tyr  Gly  Gly
1                   5

( 2 ) INFORMATION FOR SEQ ID NO:3:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Gly  Xaa  Xaa  Gly  Xaa  Xaa
1                   5